US009957218B2

(12) United States Patent
Tessonnier et al.

(10) Patent No.: US 9,957,218 B2
(45) Date of Patent: May 1, 2018

(54) ISOMERIZATION OF MUCONIC ACID

(71) Applicant: Iowa State University Research Foundation, Inc., Ames, IA (US)

(72) Inventors: Jean-Philippe Tessonnier, Ames, IA (US); Jack M. Carraher, Ames, IA (US); Toni Pfennig, Ames, IA (US); Brent Shanks, Ames, IA (US)

(73) Assignee: IOWA STATE UNIVERSITY RESEARCH FOUNDATION, INC., Ames, IA (US)

( * ) Notice: Subject to any disclaimer, the term of this patent is extended or adjusted under 35 U.S.C. 154(b) by 0 days. days.

(21) Appl. No.: 15/347,985

(22) Filed: Nov. 10, 2016

(65) Prior Publication Data
US 2017/0129839 A1    May 11, 2017

Related U.S. Application Data

(60) Provisional application No. 62/253,468, filed on Nov. 10, 2015.

(51) Int. Cl.
C07C 51/353 (2006.01)
C07D 493/04 (2006.01)

(52) U.S. Cl.
CPC .......... *C07C 51/353* (2013.01); *C07D 493/04* (2013.01); *C07B 2200/09* (2013.01)

(58) Field of Classification Search
None
See application file for complete search history.

(56) References Cited

U.S. PATENT DOCUMENTS

| 8,415,496 B2 | 4/2013 | Frost et al. | |
|---|---|---|---|
| 8,426,639 B2 | 4/2013 | Frost et al. | |
| 8,809,583 B2* | 8/2014 | Bui ..................... | C12N 9/0069 435/142 |
| 2010/0314243 A1* | 12/2010 | Frost .................... | C07C 51/353 204/157.15 |
| 2011/0124911 A1 | 5/2011 | Burk et al. | |

OTHER PUBLICATIONS

Suastegui, Miguel, et al., "Combining Metabolic Engineering and Electrocatalysis: Application to the Production of Polyamides from Sugar", *Angew. Chem. Int. Ed.*, 55, (2016), 1-7.

De Wit, G., et al., "Enolisation and isomerisation of monosaccharides in aqueous, alkaline solution", Carbohydrate Research, 74(1), (1979), 157-175.

* cited by examiner

*Primary Examiner* — Karl J Puttlitz
(74) *Attorney, Agent, or Firm* — Schwegman Lundberg & Woessner, P.A.

(57) ABSTRACT

Various embodiments disclosed relate to isomerization of muconic acid. In various embodiments, the present invention provides a method of forming trans,trans-muconic acid. The method includes heating a starting material composition to form a product composition including trans,trans-muconic acid. The starting material composition includes cis,cis-muconic acid, cis,trans-muconic acid, or a combination thereof. The starting material composition also includes an electrophilic compound, an organic solvent, or a combination thereof.

18 Claims, 16 Drawing Sheets

ISOMERIZATION OF MUCONIC ACID

CROSS-REFERENCE TO RELATED APPLICATION

This application claims the benefit of priority to U.S. Provisional Patent Application Ser. No. 62/253,468 filed Nov. 10, 2015, the disclosure of which is incorporated herein in its entirety by reference.

STATEMENT OF GOVERNMENT SUPPORT

This invention was made with Government support under EEC0813570 awarded by the National Science Foundation. The U.S. Government has certain rights in this invention.

BACKGROUND

As shown in Scheme 1, muconic acid ("MA") is an unsaturated dicarboxylic acid, hexe-2,4-dienedoic acid, which can exist in three isomeric forms.

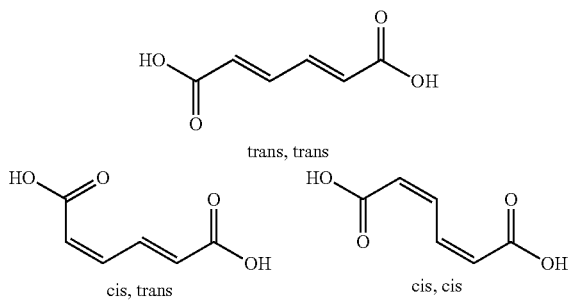

Scheme 1.

Techniques that isomerize cis,trans-muconic acid to trans,trans-muconic acid typically involve chemicals such as iodine and organic solvents or expensive noble metal catalysts (e.g., Pd/C), and require additional steps of separation and purification after isomerization to isolate the desired isomer.

SUMMARY OF THE INVENTION

In various embodiments, the present invention provides a method of forming trans,trans-muconic acid. The method includes heating a starting material composition to form a product composition including trans,trans-muconic acid. The starting material composition includes cis,cis-muconic acid, cis,trans-muconic acid, or a combination thereof. The starting material composition includes an electrophilic compound, an organic solvent, or a combination thereof.

In various embodiments, the present invention provides a method of forming trans,trans-muconic acid. The method includes heating a starting material composition to form a product composition including trans,trans-muconic acid. The starting material composition includes cis,cis-muconic acid, cis,trans-muconic acid, or a combination thereof. The starting material composition also includes a $La^{3+}$ salt.

In various embodiments, the present invention provides a method of forming trans,trans-muconic acid. The method includes heating a starting material composition to form a product composition including trans,trans-muconic acid. The starting material composition includes cis,cis-muconic acid, cis,trans-muconic acid, or a combination thereof. The starting material composition includes $AlBr_3$, $AlCl_3$, or a combination thereof, and a polar aprotic solvent.

In various embodiments, the present invention provides a method of forming trans,trans-muconic acid. The method includes heating a starting material composition to form a product composition including trans,trans-muconic acid. The starting material composition includes cis,cis-muconic acid, cis,trans-muconic acid, or a combination thereof, and dimethylsulfoxide.

In various embodiments, the present invention provides a method of forming a trans,trans-muconic acid Diels-Alder adduct. The method includes heating a starting material composition to form a product composition including trans,trans-muconic acid. The starting material composition includes cis,cis-muconic acid, cis,trans-muconic acid, or a combination thereof. The starting material composition also includes an electrophilic compound, a polar aprotic solvent, or a combination thereof. The method also includes reacting the trans,trans-muconic acid with a dienophile, to form a Diels-Alder adduct.

In various embodiments, the present invention provides a method of forming trans,trans-muconic acid. The method includes heating a starting material composition to form a product composition including trans,trans-muconic acid. The starting material composition includes cis,cis-muconic acid, cis,trans-muconic acid, or a combination thereof. The starting material composition includes dimethylsulfoxide (DMSO). The starting material composition also includes about 0 wt % to about 20 wt % water. $D_2O$, or a combination thereof. The starting material composition is substantially free of solvents other than the DMSO and the water and $D_2O$.

In various embodiments, the present invention provides a method of cycloaddition. The method includes performing a Diels-Alder reaction on a reaction mixture. The reaction mixture includes diene trans,trans-muconic acid and dienophile substituted or unsubstituted ethylene. The Diels-Alder reaction forms a Diels-Alder adduct. The Diels-Alder reaction is performed at elevated temperatures, in γ-valerolactone (GVL), in dioxane, or a combination thereof. The Diels-Alder adduct is a substituted or unsubstituted cyclohex-1-ene-1,4-dicarboxylic acid and substantially no substituted or unsubstituted cyclohex-2-ene-1,4-dicarboxylic acid is formed.

In various embodiments, the method of isomerizing muconic acid can have advantages over other methods of forming trans,trans-muconic acid, at least some of which are unexpected. For example, in some embodiments, the present method can be performed without iodine or other organic solvents, or can be performed using less organic solvents or other toxic materials than other methods of forming trans,trans-muconic acid. In various embodiments, the present method of isomerizing muconic acid to form trans,trans-muconic acid can be performed in an aqueous solution using a solid catalyst (e.g., a heterogeneous reaction). In various embodiments, the trans,trans-muconic acid formed by the present method can be used directly in a Diels-Alder reaction without purification or with less purification than other methods.

In some embodiments, the present method can be a more efficient and more effective way to generate trans,trans-muconic acid and products derivable therefrom than other methods. In some embodiments, the present method can have a higher selectivity of trans,trans-muconic acid from cis,trans-muconic acid, from cis,cis-muconic acid, or a combination thereof, than other methods. In some embodiments, the present method can have a higher percent conversion of starting materials than other methods, such as a higher conversion of cis,trans-muconic acid, of cis,cis-muconic acid, or of a combination thereof.

In various embodiments, the present method can provide an efficient way to form the Diels-Alder-active diene trans,trans-muconic acid. In various embodiments, the produced trans,trans-muconic acid can be reacted with ethylene in a Diels-Alder reaction to form a Diels-Alder adduct, a cyclohexene-1,4-dicarboxylic acid. The cyclohexene-1,4-dicarboxylic acid can be hydrogenated to provide cyclohexane-1,4-dicarboxylic acid. Alternatively, the Diels-Alder adduct can then be aromatized to provide terephthalic acid. In various embodiments, the present method can provide a more economical, more efficient, and more environmentally-friendly route to terephthalic acid than other methods, including as compared to other methods that start with muconic acid. In various embodiments, the terephthalic acid can be polymerized to form polyethylene terephthalate (PET), providing a more economical, more efficient, and more environmentally-friendly route to PET than other methods.

In various embodiments, the present method can be performed using DMSO, which is advantageously a cheap, readily available solvent that has lower toxicity (e.g., LD50) than ethanol. In various embodiments. DMSO can be used as a solvent without the presence of a catalyst (e.g., no electrophile), advantageously avoiding the need for a catalyst. Isomers of muconic acid are highly soluble in DMSO, allowing performance of a subsequent reaction step such as a Diels-Alder reaction with minimal or no purification or separation steps, providing a more efficient way to produce and use trans,trans-muconic acid.

BRIEF DESCRIPTION OF THE FIGURES

The drawings illustrate generally, by way of example, but not by way of limitation, various embodiments discussed in the present document.

DETAILED DESCRIPTION OF THE INVENTION

Figure 1:
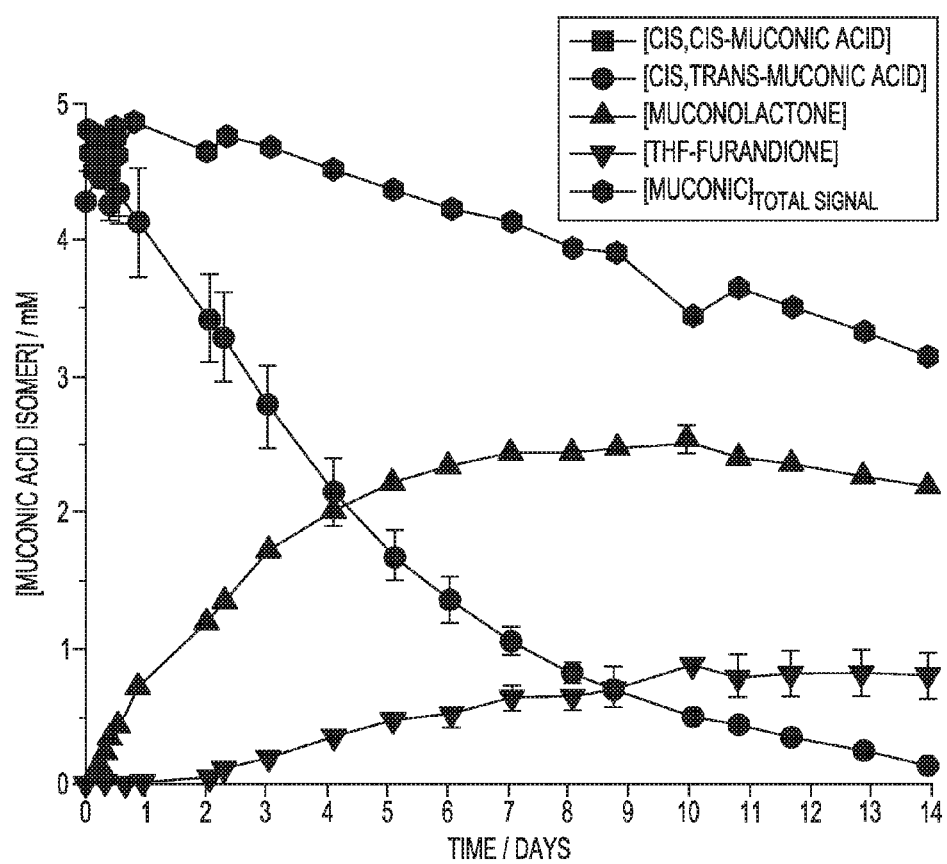
FIG. 1 illustrates the concentration of isomers and products when cis,trans-muconic acid was heated at 75° C. in $D_2O$ for 14 days, in accordance with various embodiments. No trans,trans-muconic acid was observed.

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z." unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. A comma can be used as a delimiter or digit group separator to the left or right of a decimal mark; for example, "0.000,1"

is equivalent to "0.0001." All publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods described herein, the acts can be carried out in any order without departing from the principles of the invention, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range, and includes the exact stated value or range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%. The term "substantially free of" can mean having a trivial amount of, such that a composition is about 0 wt % to about 5 wt % of the material, or about 0 wt % to about 1 wt %, or about 5 wt % or less, or less than, equal to, or greater than about 4.5 wt %, 4, 3.5, 3, 2.5, 2, 1.5, 1.0.9, 0.8, 0.7, 0.6, 0.5, 0.4, 0.3, 0.2, 0.1, 0.01, or about 0.001 wt % or less, or about 0 wt %.

The term "organic group" as used herein refers to any carbon-containing functional group. Examples can include an oxygen-containing group such as an alkoxy group, aryloxy group, aralkyloxy group, oxo(carbonyl) group; a carboxyl group including a carboxylic acid, carboxylate, and a carboxylate ester; a sulfur-containing group such as an alkyl and aryl sulfide group; and other heteroatom-containing groups. Non-limiting examples of organic groups include OR, OOR, OC(O)N(R)$_2$, CN, CF$_3$, OCF$_3$, R, C(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, C(=NOR)R, and substituted or unsubstituted (C$_1$-C$_{100}$)hydrocarbyl, wherein R can be hydrogen (in examples that include other carbon atoms) or a carbon-based moiety, and wherein the carbon-based moiety can be substituted or unsubstituted.

The term "substituted" as used herein in conjunction with a molecule or an organic group as defined herein refers to the state in which one or more hydrogen atoms contained therein are replaced by one or more non-hydrogen atoms. The term "functional group" or "substituent" as used herein refers to a group that can be or is substituted onto a molecule or onto an organic group. Examples of substituents or functional groups include, but are not limited to, a halogen (e.g., F, Cl, Br, and I); an oxygen atom in groups such as hydroxy groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxyamines, nitriles, nitro groups. N-oxides, hydrazides, azides, and enamines; and other heteroatoms in various other groups. Non-limiting examples of substituents that can be bonded to a substituted carbon (or other) atom include F, Cl, Br, I, OR, OC(O)N(R)$_2$, CN, NO, NO$_2$, ONO$_2$, azido, CF$_3$, OCF$_3$, R, O (oxo), S (thiono), C(O), S(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, and C(=NOR)R, wherein R can be hydrogen or a carbon-based moiety; for example, R can be hydrogen, (C$_1$-C$_{100}$)hydrocarbyl, alkyl, acyl, cycloalkyl, aryl, aralkyl, heterocyclyl, heteroaryl, or heteroarylalkyl; or wherein two R groups bonded to a nitrogen atom or to adjacent nitrogen atoms can together with the nitrogen atom or atoms form a heterocyclyl.

The term "alkyl" as used herein refers to straight chain and branched alkyl groups and cycloalkyl groups having from 1 to 40 carbon atoms, 1 to about 20 carbon atoms, 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl n-heptyl, and n-octyl groups. Examples of branched alkyl groups include, but are not limited to, isopropyl, iso-butyl, sec-butyl, t-butyl, neo-pentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "alkenyl" as used herein refers to straight and branched chain and cyclic alkyl groups as defined herein, except that at least one double bond exists between two carbon atoms. Thus, alkenyl groups have from 2 to 40 carbon atoms, or 2 to about 20 carbon atoms, or 2 to 12 carbon atoms or, in some embodiments, from 2 to 8 carbon atoms. Examples include, but are not limited to, vinyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, cyclohexenyl, cyclopentenyl, cyclohexadienyl, butadienyl, pentadienyl, and hexadienyl among others.

The term "acyl" as used herein refers to a group containing a carbonyl moiety wherein the group is bonded via the carbonyl carbon atom. The carbonyl carbon atom is bonded to a hydrogen forming a "formyl" group or is bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. An acyl group can include 0 to about 12, 0 to about 20, or 0 to about 40 additional carbon atoms bonded to the carbonyl group. An acyl group can include double or triple bonds within the meaning herein. An acryloyl group is an example of an acyl group. An acyl group can also include heteroatoms within the meaning herein. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "aryl" as used herein refers to cyclic aromatic hydrocarbon groups that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined herein. Representative substituted aryl groups can be mono-substituted or substituted more than once, such as, but not limited to, a phenyl group substituted at any one or more of 2-, 3-, 4-, 5-, or 6-positions of the phenyl ring, or a naphthyl group substituted at any one or more of 2- to 8-positions thereof.

The terms "halo." "halogen," or "halide" group, as used herein, by themselves or as part of another substituent, mean, unless otherwise stated, a fluorine, chlorine, bromine, or iodine atom.

The term "haloalkyl" group, as used herein, includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, and the like.

The term "hydrocarbon" or "hydrocarbyl" as used herein refers to a molecule or functional group, respectively, that includes carbon and hydrogen atoms. The term can also refer to a molecule or functional group that normally includes both carbon and hydrogen atoms but wherein all the hydrogen atoms are substituted with other functional groups.

As used herein, the term "hydrocarbyl" refers to a functional group derived from a straight chain, branched, or cyclic hydrocarbon, and can be alkyl, alkenyl, alkynyl, aryl, cycloalkyl, acyl, or any combination thereof. Hydrocarbyl groups can be shown as $(C_a-C_b)$hydrocarbyl, wherein a and b are integers and mean having any of a to b number of carbon atoms. For example, $(C_1-C_4)$hydrocarbyl means the hydrocarbyl group can be methyl $(C_1)$, ethyl $(C_2)$, propyl $(C_3)$, or butyl $(C_4)$, and $(C_0-C_b)$hydrocarbyl means in certain embodiments there is no hydrocarbyl group.

The term "solvent" as used herein refers to a liquid that can dissolve a solid, liquid, or gas. Non-limiting examples of solvents are silicones, organic compounds, water, alcohols, ionic liquids, and supercritical fluids.

The term "room temperature" as used herein refers to a temperature of about 15° C. to 28° C.

In various embodiments, salts having a positively charged counterion can include any suitable positively charged counterion. For example, the counterion can be ammonium $(NH_4^+)$, or an alkali metal such as sodium $(Na^+)$, potassium $(K^+)$, or lithium $(Li^+)$. In some embodiments, the counterion can have a positive charge greater than +1, which can in some embodiments complex to multiple ionized groups, such as $Zn^{2+}$, $Al^{3+}$, or alkaline earth metals such as $Ca^{2+}$ or $Mg^{2+}$.

In various embodiments, salts having a negatively charged counterion can include any suitable negatively charged counterion. For example, the counterion can be a halide, such as fluoride, chloride, iodide, or bromide. In other examples, the counterion can be nitrate, hydrogen sulfate, dihydrogen phosphate, bicarbonate, nitrite, perchlorate, iodate, chlorate, bromate, chlorite, hypochlorite, hypobromite, cyanide, amide, cyanate, hydroxide, permanganate. The counterion can be a conjugate base of any carboxylic acid, such as acetate or formate. In some embodiments, a counterion can have a negative charge greater than −1, which can in some embodiments complex to multiple ionized groups, such as oxide, sulfide, nitride, arsenate, phosphate, arsenite, hydrogen phosphate, sulfate, thiosulfate, sulfite, carbonate, chromate, dichromate, peroxide, or oxalate.

Method of Preparing Trans,Trans-Muconic Acid.

In various embodiments, the present invention provides method of forming trans,trans-muconic acid. The method can include heating a starting material composition to form a product composition including trans,trans-muconic acid. The starting material composition can include cis,cis-muconic acid, cis,trans-muconic acid, or a combination thereof. The starting material composition can also include an electrophilic compound, an organic solvent, or a combination thereof.

Isomerization methods to form trans,trans-muconic acid herein are not electrocatalytic or electrochemical methods. Therefore, in various embodiments, the heating of the starting material to form the product composition, and the chemical mechanism of the isomerization to form the trans,trans-muconic acid, can be free of electrochemical reactions.

The muconic acid can be produced in any suitable way. In some embodiments, the muconic acid is commercially obtained. In some embodiments, the muconic acid is produced from petroleum materials. In some embodiments, the muconic acid is produced from a microorganism or an enzyme, such as any suitable microorganism or enzyme. The muconic acid can be produced by yeast or bacteria, such as any suitable yeast or bacteria. The microorganism (e.g., yeast or bacteria) or enzyme can use any suitable organic material to generate the muconic acid, such as a carbohydrate (e.g., glucose), or such as an aromatic material (e.g., lignin). In some embodiments, the muconic acid is generated by yeast in a fermentation broth.

The muconic acid starting material can be any suitable muconic acid. The muconic acid can be cis,cis-muconic acid, cis,trans-muconic acid, or a combination thereof. In some embodiments, the muconic starting material can also include trans,trans-muconic acid, provided that the product composition has a higher concentration of trans,trans-muconic acid than the starting material composition. In various embodiments, the muconic acid starting material is about 0 mol % to about 100 mol % cis,cis-muconic acid, or about 0 mol %, or about 0.001 mol % or less, or less than, equal to, or more than about 0.01 mol %, 0.1, 1, 2, 3, 4, 5, 6, 8, 10, 12, 14, 16, 18, 20, 25, 30, 35, 40, 45, 50, 55, 60, 65, 70, 75, 80, 82, 84, 86, 88, 90, 91, 92, 93, 94, 95, 96, 97, 98, 99, 99.9, 99.99, or about 99.999 mol % or more, or about 100 mol %, In various embodiments, the muconic acid starting material is about 0 mol % to about 100 mol % cis,trans-muconic acid, or about 0 mol %, or about 0.001 mol % or less, or less than, equal to, or more than about 0.01 mol %, 0.1, 1, 2, 3, 4, 5, 6, 8, 10, 12, 14, 16, 18, 20, 25, 30, 35, 40, 45, 50, 55, 60, 65, 70, 75, 80, 82, 84, 86, 88, 90, 91, 92, 93, 94, 95, 96, 97, 98, 99, 99.9, 99.99, or about 99.999 mol % or more, or about 100 mol %. In various embodiments, the muconic acid starting material is about 0 mol % to about 99.999 mol % trans,trans-muconic acid, or about 0 mol %, or about 0.001 mol % or less, or less than, equal to, or more than about 0.01 mol %, 0.1, 1, 2, 3, 4, 5, 6, 8, 10, 12, 14, 16, 18, 20, 25, 30, 35, 40, 45, 50, 55, 60, 65, 70, 75, 80, 82, 84, 86, 88, 90, 91, 92, 93, 94, 95, 96, 97, 98, 99, 99.9, 99.99, or about 99.999 mol % or more.

In some embodiments, the concentration of the cis,cis-muconic acid and the cis,trans-muconic acid (wherein either one or both can be present) in the starting material composition can be about 0.000001 g/L to about 350 g/L, or about 0.1 g/L to about 300 g/L, or about 0.000001 g/L or less, or less than, equal to, or greater than about 0.00001 g/l, 0.0001, 0.001, 0.01, 0.1, 1, 2, 3, 4, 5, 6, 8, 10, 12, 14, 16, 18, 20, 25, 30, 35, 40, 45, 50, 60, 70, 80, 90, 100, 125, 150, 175, 200, 225, 250, 275, 300, 325, or about 350 g/L or more.

The starting material composition can include any suitable solvent. In some embodiments, the starting material composition can be aqueous, with water as a solvent. An aqueous starting material composition can include any suitable wt % water, such as about 0.01 wt % to about 99.99 wt %, or about 0.01 wt % or less, or less than, equal to, or more than 0.1 wt %, 1, 2, 3, 4, 5, 10, 15, 20, 25, 30, 35, 40, 45, 50, 55, 60, 65, 70, 75, 80, 85, 90, 91, 92, 93, 94, 95. 96, 97, 98, 99, 99.9, or about 99.99 wt % or more. An aqueous starting material composition can be substantially free of solvents other than water.

An organic solvent in the starting material composition can be any suitable one or more organic solvent. The one or more organic solvents can be any suitable wt % of the starting material composition, such as about 0.01 wt % to about 99.99 wt %, or about 0.01 wt % or less, or less than, equal to, or more than 0.1 wt %, 1, 2, 3, 4, 5, 10, 15, 20, 25, 30, 35, 40, 45, 50, 55, 60, 65, 70, 75, 80, 85, 90, 91, 92, 93, 94, 95, 96, 97, 98, 99, 99.9, or about 99.99 wt % or more. The one or more polar aprotic solvents can be substantially free of other solvents, or the one or more polar aprotic solvents can include other solvents (e.g., water. $D_2O$, or a combination thereof). The one or more organic solvents can be polar solvents, polar protic solvents (e.g., including an —OH group, such as a ($C_1$-$C_{10}$)alcohol, such as methanol, ethanol, or propanol), polar aprotic solvents (e.g., free of an —OH group), nonpolar solvents (e.g., hexane, toluene), or a combination thereof.

In some embodiments, the starting material composition can include methanol, ethanol, 2-propanol, hexanol, toluene, or a combination thereof.

In some embodiments, the starting material composition can include a polar aprotic solvent (e.g., wherein "aprotic" indicates a material that is free of —OH bonds). For example, the starting material composition can include dimethylsulfoxide (DMSO), acetonitrile ($CH_3CN$), tetrahydrofuran (THF), ethyl acetate (EtOAc), dimethylformamide (DMF). γ-valerolactone (GVL), or a combination thereof. The one or more polar aprotic solvents can be any suitable wt % of the starting material composition, such as about 0.01 wt % to about 99.99 wt %, or about 0.01 wt % or less, or less than, equal to, or more than 0.1 wt %, 1, 2, 3, 4, 5, 10, 15, 20, 25, 30, 35, 40, 45, 50, 55, 60, 65, 70, 75, 80, 85, 90, 91, 92, 93, 94, 95, 96, 97, 98, 99, 99.9, or about 99.99 wt % or more. The one or more polar aprotic solvents can be substantially free of other solvents. For example, the one or more polar aprotic solvents can be substantially free of protic solvents (e.g., water), can be substantially free of nonpolar aprotic solvents, or a combination thereof.

In various embodiments, the organic solvent is dimethylsulfoxide (DMSO). In embodiments including DMSO as the organic solvent, the starting material composition can optionally be substantially free of the electrophilic compound. In addition to DMSO, the starting material composition can optionally include water, $D_2O$, or a combination thereof, or the starting material composition can be free of water. The starting material composition can be substantially free of solvents other than DMSO and water or $D_2O$. About 0.000001 wt % to about 20 wt % of the starting material composition can be water. $D_2O$, or a combination thereof, or about 0.00001 to about 2 wt %, or about 0.000001 wt % or less, or less than, equal to, or greater than about 0.00001 wt %, 0.0001, 0.001, 0.01, 0.1, 1, 2, 3, 4, 5, 6, 7, 8, 9, 10, 11, 12, 13, 14, 15, 16, 17, 18, 19, or about 20 wt % or more. At combined concentrations of the cis,cis-muconic acid and cis,trans-muconic acid equal to or greater than about 0.7 g/L muconolactone can be produced; however, with the addition of about 1 to about 20 molar equivalents of water, $D_2O$, or a combination thereof the reaction pathway can shift back to yield primary trans,trans-muconic acid. For example, the starting material composition can be about 1 to about 20 molar equivalents of water or $D_2O$ relative to total moles of cis,cis-muconic acid and cis,trans-muconic acid, or about 3 to 10, or about 1 or less, or less than, equal to, or greater than about 2, 3, 4, 5, 6, 7, 8, 9, 10, 11, 12, 13, 14, 15, 16, 17, 18, 19, or about 20 molar equivalents or more. The use of $D_2O$ can help to avoid lactonization and improve selectivity to the trans,trans-muconic acid, especially at high starting concentrations of cis,cis-muconic acid or cis,trans-muconic acid.

The starting material composition can include one electrophilic compound, more than one electrophilic compound, or can be substantially free of the electrophilic compound. The electrophilic compound can be any suitable electrophilic compound, such as an electrophilic compound that has an affinity for (e.g., can coordinate with) a carboxylate group (e.g., —$CO_2^-$). The electrophilic compound can be a Lewis acid, such as any suitable Lewis acid. The Lewis acid can include or can be $Li^+$, $Na^+$, $K^+$, $BeMe_2$, $Be^{2+}$, RMgX, $Mg^{2+}$, $Ca^{2+}$, $Sr^{2+}$, $AlCl_3$, $AlMe_3$, $AlHl_3$, $Al(OR)_3$, $Al^{3+}$, $GaMe_3$, $InMe_3$, $In^{3+}$, $SnR_3^+$, $SnMe_2^{2+}$, $Sn^{2+}$, $Sc^{3+}$, $La^{3+}$, $Ti(OR)_4$, $Ti^{4+}$, $Zr^{4+}$, $VO_2^+$, $Cr^{3+}$, $Fe^{3+}$, $Co^{3+}$, $Ir^{3+}$, $Th^{4+}$, $UO_2^{2+}$, $Pu^{4+}$, $Yb^{3+}$, $GaH_3$, $Sn(OR)_4$, $SnCl_4$, $Pb^{2+}$, $Sb^{2+}$, $Bi^{3+}$, $Sc(OTf)_3$, $ScCl_3$, $Fe^{2+}$, $Co^{2+}$, $Ni^{2+}$, $Cu^{2+}$, $RZn^+$, $Zn^{2+}$, $Yb(OTf)_3$, $YbCl_3$, $Cs^+$, $TlMe_3$, $Tl^+$, $Tl^{3+}$, $Pd(PAr_3)_2$, $Pd(PAr_3)_2^+$, $Pd^{2+}$, $Pt^{2+}$, $Cu^+$, $Ag^+$, $Au^+$, $CdR^+$, $Cd^{2+}$, $HgR^+$, $Hg^+$, $Hg^{2+}$, $B(OR)_3$, $BF_3$, $BCl_3$, $R_3Si^+$, $Si^{4+}$, $As^{3+}$, $SO_3$, $BR_3$, $BH_3$, a salt thereof, or a combination thereof, wherein at each occurrence R is independently substituted or unsubstituted ($C_1$-$C_{20}$)hydrocarbyl. In some embodiments, the Lewis acid is a $La^{3+}$ salt, such as $LaCl_3$, $LaBr_3$, $La(OH)_3$, or a combination thereof. The electrophilic compound can be $LaBr_3$ (e.g., anhydrous, or as a hydrate such as $LaBr_3 \times 6H_2O$).

The heating can be any suitable heating such that a product composition including trans,trans-muconic acid is formed. The heating can include maintaining the starting material composition at reflux. The heating can include maintaining the starting material composition at greater than room temperature to about 300° C., or about 50° C. to about 110° C., 50° C. to about 130° C., or about 30° C. 35, 40, 45, 50, 55, 60, 65, 70, 75, 80, 85, 90, 95, 100, 105, 110, 115, 120, 125, 130, 140, 150, 160, 170, 180, 190, 200, 225, 250, 275° C., or about 300° C. or more. The heating can be performed for any suitable duration, such as about 0.01 min to about 100 days, about 1 day to about 30 days, about 1 hour to about 2 days, or about 0.01 min or less, or less than, equal to, or greater than about 0.1 min, 0.5, 1, 2, 3, 4, 5, 10, 15, 20, 25, 30, 35, 40, 45, 50, 55 min, 1 h, 1.5, 2, 2.5, 3, 3.5, 4, 4.5, 5, 6, 7, 8, 9, 10, 11, 12, 13, 14, 15, 16, 17, 18, 19, 20, 21, 22, 23 h, 1 d, 1.5, 2, 2.5, 3, 4, 5, 6, 7, 8, 10, 12, 14, 16, 18, 20, 25, 30, 35, 40, 45, 50, 55 d, or about 60 d or more.

The method of forming the product composition from the starting material composition can have any suitable percent conversion of the cis,cis-muconic acid, the cis,trans-muconic acid, or a combination thereof, in the starting material composition, such as about 0.01% to about 100%, about 50% to about 95%, 80% to about 90%, or about 0.01% or less, or less than, equal to, or greater than about 0.1%, 1, 2, 3, 4, 5, 6, 8, 10, 12, 14, 16, 18, 20, 25, 30, 35, 40, 45, 50, 55, 60, 65, 70, 75, 80, 82, 84, 86, 88, 90, 91, 92, 93, 94, 95, 96, 97, 98, 99, 99.9, or about 99.99% or more.

The method can form the product composition with any suitable selectivity of conversion of the cis,cis-muconic acid, the cis,trans-muconic acid, or a combination thereof, in the starting material composition to the trans,trans-muconic acid in the product composition, such as about 0.01% to about 100%, about 50% to about 95%, or about 0.01% or less, or less than, equal to, or greater than about 0.1%, 1, 2, 3, 4, 5, 6, 8, 10, 12, 14, 16, 18, 20, 25, 30, 35, 40, 45, 50, 55, 60, 65, 70, 75, 80, 82, 84, 86, 88, 90, 91, 92, 93, 94, 95, 96, 97, 98, 99, 99.9, or about 99.99% or more.

The yield of the trans,trans-muconic acid in the product composition from the cis,cis-muconic acid, the cis,trans-muconic acid, or a combination thereof, in the starting material composition can be any suitable yield, such as about 0.01% to about 100%, about 40% to about 80%, about 40% to about 60%, or about 0.01% or less, or less than, equal to, or greater than about 0.1%, 1, 2, 3, 4, 5, 6, 8, 10, 12, 14, 16, 18, 20, 25, 30, 35, 40, 45, 50, 55, 60, 65, 70, 75, 80, 82, 84, 86, 88, 90, 91, 92, 93, 94, 95, 96, 97, 98, 99, 99.9, or about 99.99% or more.

The starting material composition can include a fermentation broth including the cis,trans-muconic acid of cis,cis-muconic acid. The fermentation broth can be any suitable fermentation broth. The fermentation broth can include glucose and support the conversion of glucose into muconic acid by yeast, such as any suitable type of yeast that can perform the conversion. The fermentation broth can include yeast nitrogen base. The yeast nitrogen base can be substantially free of amino acids, ammonium sulfate, or a combination thereof. The fermentation broth can include complete supplement mixture (CSM) uracil-dropout amino acid mix. The method can include at least partially simultaneously fermenting the broth to form cis,trans-muconic acid, cis,cis-muconic acid, or a combination thereof, from the yeast and isomerizing the muconic acid in the broth.

Method of Preparing Terephthalic Acid.

In various embodiments, the present invention provides a method of preparing substituted or unsubstituted terephthalic acid. Trans,trans-muconic acid is a suitable dienophile for a Diels-Alder reaction. In various embodiments, the method includes reacting the trans,trans-muconic acid with a Diels-Alder dienophile to form a Diels-Alder adduct.

The Diels-Alder dienophile can be any suitable dienophile. The Diels-Alder dienophile can be a substituted or unsubstituted ethylene, wherein the Diels-Alder adduct is a tetrahydrogenated substituted or unsubstituted terephthalic acid.

The method can include hydrogenating the Diels-Alder adduct to provide a substituted or unsubstituted cyclohexane-1,4-dicarboxylic acid, such as over any suitable hydrogenation catalyst.

The method can further include aromatizing the Diels-Alder adduct (e.g., dehydrogenating, such as to remove 4 hydrogen atoms from the tetahydrogenated ring of the Diels-Alder adduct), to provide an aromatic compound. For example, the dienophile can be a substituted or unsubstituted ethylene, and the aromatized Diels-Alder adduct can be a substituted or unsubstituted terephthalic acid. For example, the dienophile can be an unsubstituted ethylene, and the aromatized Diels-Alder adduct can be terephthalic acid. The aromatization can be performed using any suitable dehydrogenation reagents, such as using Pd/C.

The Diels-Alder reaction can be performed in DMSO. In some embodiments, the isomerization can be performed in DMSO, such as in the absence of the electrophilic compound, optionally including some amount of water or $D_2O$, and the Diels-Alder reaction can be subsequently performed with little or no separation or purification after the isomerization.

In some embodiments, the Diels-Alder reaction can be performed at elevated temperatures, in γ-valerolactone (GVL), or in dioxane, the dienophile can be a substituted or unsubstituted ethylene, and the Diels-Alder adduct can be a substituted or unsubstituted cyclohex-1-ene-1,4-dicarboxylic acid and substantially no substituted or unsubstituted cyclohex-2-ene-1,4-dicarboxylic acid is formed.

The method can include esterifying the trans,trans-muconic acid (e.g., $(C_{1-10})$alkyl ester, such as methyl or ethyl, or using ethylene glycol, propylene glycol, polyethylene glycol, or polypropylene glycol) and reacting the esterification product with a Diels-Alder dienophile to form a Diels-Alder adduct. Such esterification can prevent isomerization of the Diels-Alder product. The dienophile can be a substituted or unsubstituted ethylene, and the Diels-Alder adduct is a substituted or unsubstituted cyclohex-2-ene-1,4-dicarboxylic acid with substantially no formation of substituted or unsubstituted cyclohex-1-ene-1,4-dicarboxylic acid.

Method of Preparing Polyethylene Terephthalate.

In various embodiments, the present invention includes polymerizing a Diels-Alder adduct formed from the trans,trans-muconic acid (e.g., an unaromatized product). The Diels-Alder adduct can be polymerized with any suitable material, such as ethylene glycol, to provide a polymer. In some embodiments, the resulting polymer can be subsequently vulcanized.

In various embodiments, the present invention provides a method of preparing polyethylene terephthalate. The method can include forming the trans,trans-muconic acid, reacting the trans,trans-muconic acid with substituted (e.g., with electron-withdrawing groups) or unsubstituted ethylene to form a Diels-Alder adduct, aromatizing the Diels-Alder adduct to give a substituted or unsubstituted terephthalic acid, and polymerizing the substituted or unsubstituted terephthalic acid with substituted or unsubstituted ethylene glycol to give a substituted or unsubstituted polyethylene terephthalate. In some embodiments, the dienophile is unsubstituted ethylene, and the ethylene glycol is unsubstituted, such that the aromatized product is unsubstituted terephthalic acid, and the polymer is unsubstituted polyethylene terephthalate.

EXAMPLES

Various embodiments of the present invention can be better understood by reference to the following Examples which are offered by way of illustration. The present invention is not limited to the Examples given herein.

Part 1. Aqueous Isomerization of Muconic Acid.

Example 1-1. Isomerization of Muconic Acid (MA) in Water

Cis,cis-muconic acid (ccMA) was isomerized to cis,trans-muconic acid within 20 minutes at 83° C. in water. However, trans,trans-muconic acid (ttMA) was never observed, even at higher temperature. Instead, cis,trans-muconic acid (ctMA) undergoes ring closing reactions to form muconolactone (Mlac) and the corresponding dilactone, as shown in Scheme 2. The primary cause of ring closure is a strong intramolecular interaction between the cis-carboxyl group and interior (alkene) carbons.

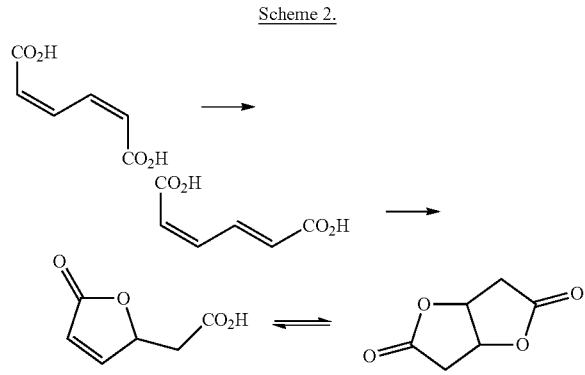

Scheme 2.

FIG. 1 illustrates the concentration of isomers and products when cis,trans-muconic acid was heated at 75° C. in $D_2O$ for 14 days.

Example 1-2. Isomerization of Muconic Acid in Water at Various pH

Figure 2:
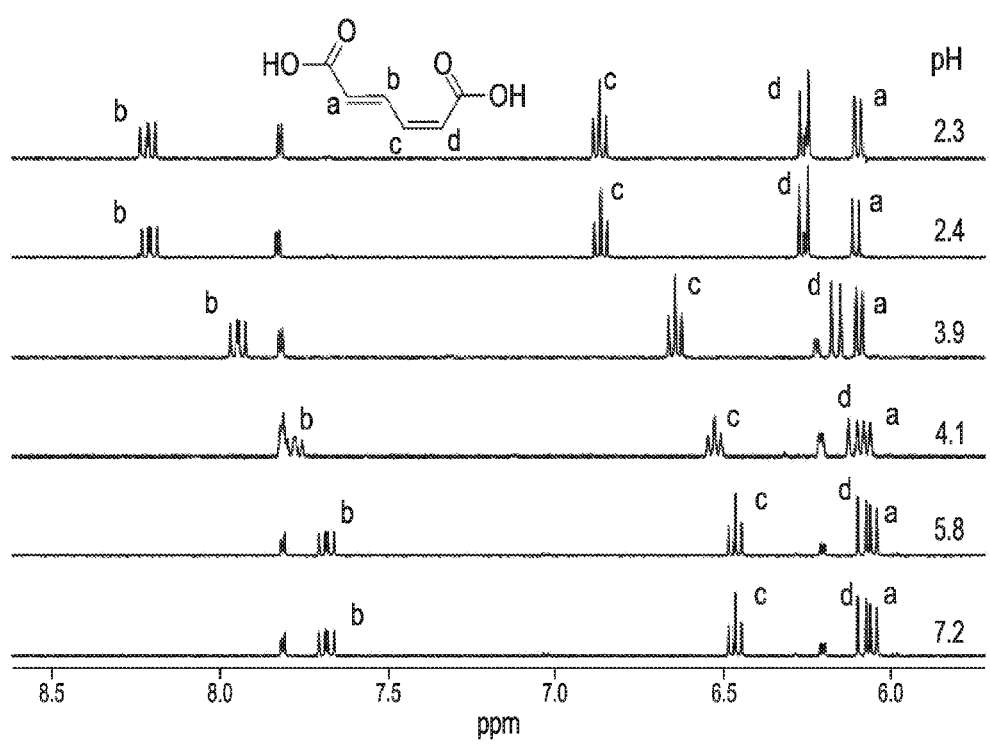
FIG. 2 illustrates a $^1H$ NMR showing the shift of various hydrogen atoms in cis,trans-muconic acid and in muconolactone in $D_2O$ at various pH.

It is hypothesized that formation of muconolactone and the corresponding dilactone instead of trans,trans-muconic acid is due to strong intramolecular interactions between carboxyl groups and interior carbons. FIG. 2 illustrates a $^1H$ NMR showing the shift of various hydrogen atoms in cis,trans-muconic acid and in muconolactone in $D_2O$ at various pH.

Example 1-3. Computational Study

Figure 3:
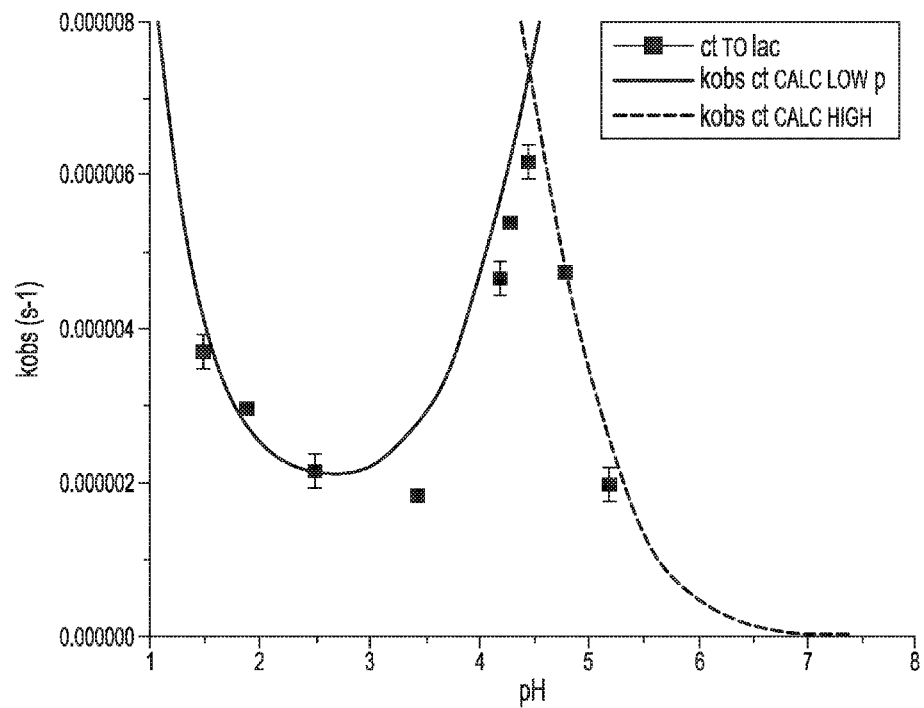
FIG. 3 illustrates the observed and calculated rate of muconolactone formation at various pH, in accordance with various embodiments.

With rate of muconolactone formation=$k_{obs}$[MA], FIG. 3 illustrates $k_{obs}$ versus pH, including calculated $k_{obs}$ and actual $k_{obs}$ at various pH.

Values for $k_{obs}$ were obtained experimentally, using aqueous solutions of cis,trans-muconic acid with pH values of about 1 to about 8, and with temperatures of about 50° C. to about 90° C. Then, based on the pH trends and concentration dependencies observed, elementary equations were used to formulate approximations for $k_{obs}$ at either low pH or high pH. These approximations were fitted to the experimental data, and the rate constants from the fit were input into a kinetics simulation software (KINSIM) and adjusted further until satisfactory agreement was found for both individual kinetic traces and for the $k_{obs}$ vs pH profile plot.

Figure 4:
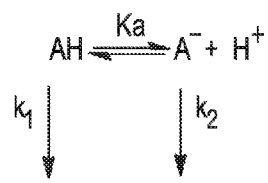
FIG. 4 illustrates a reaction, according to various embodiments.

For the line on the left of FIG. 3, the equation shown in Scheme 3 was used to compute $k_{obs}$ for the reaction shown in FIG. 4.

$$k_{obs} = \frac{[H^+] \times k_1 + Ka \times k_2}{[H^+] + Ka}. \quad \text{Scheme 3}$$

Figure 5:
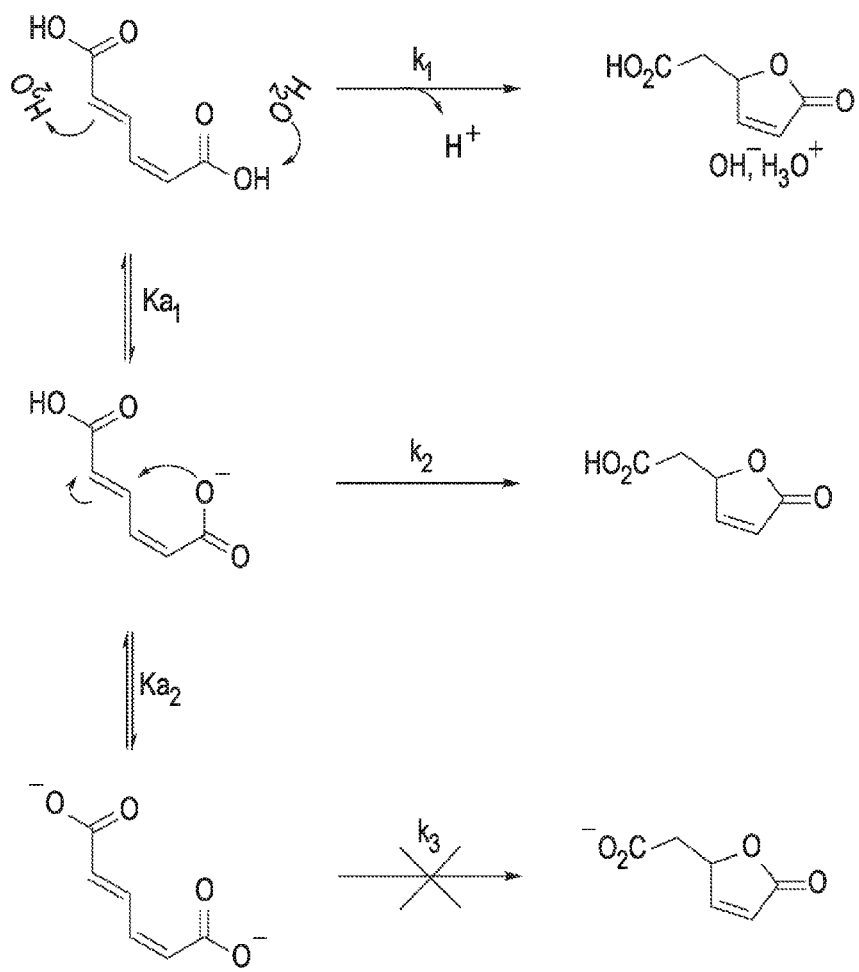
FIG. 5 illustrates a reaction scheme, in accordance with various embodiments.

For the line on the right of FIG. 3, the equation shown in Scheme 4 was used to compute $k_{obs}$ for the reaction shown in FIG. 5.

$$k_{obs} = \frac{[H^+] \times k_1 + Ka_1 \times k_2}{[H^+] + Ka_1} + \frac{[H^+] \times k_2 + Ka_2 \times k_3}{[H^+] + Ka_2}. \quad \text{Scheme 4B}$$

Figure 6:
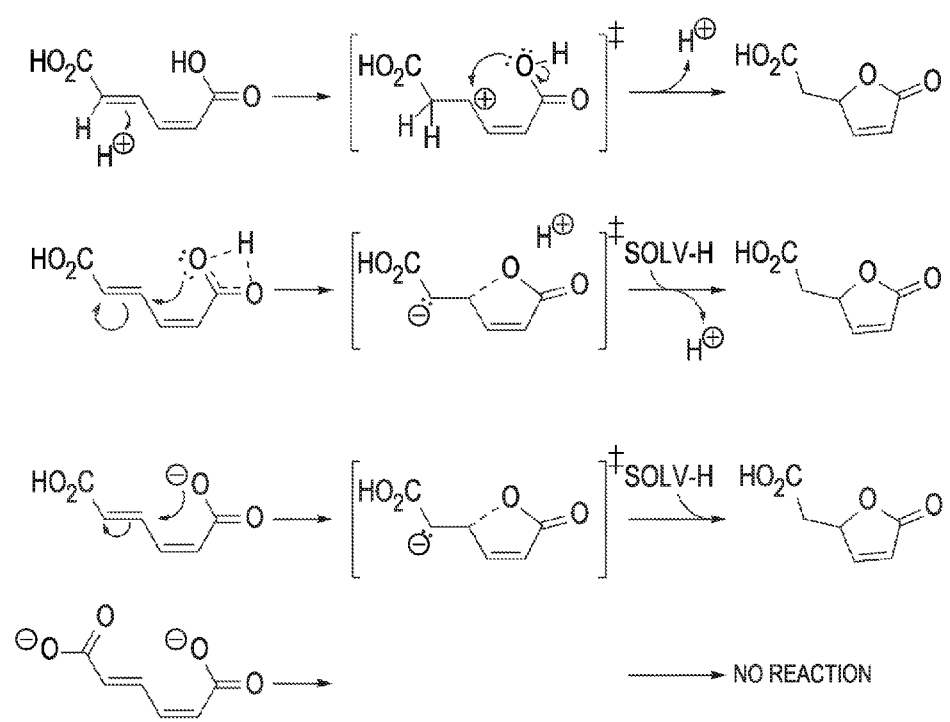
FIG. 6 illustrates isomerization pathways, in accordance with various embodiments.

The huge changes in kinetics with changes in pH indicate that ctMAH$^-$ is most active form. Also, H$^+$ catalyzes the isomerization pathway, as shown in FIG. 6. No ttMA was observed at any pH.

Part 2. Lanthanum Tribromide.

Example 2-1

Figure 7:
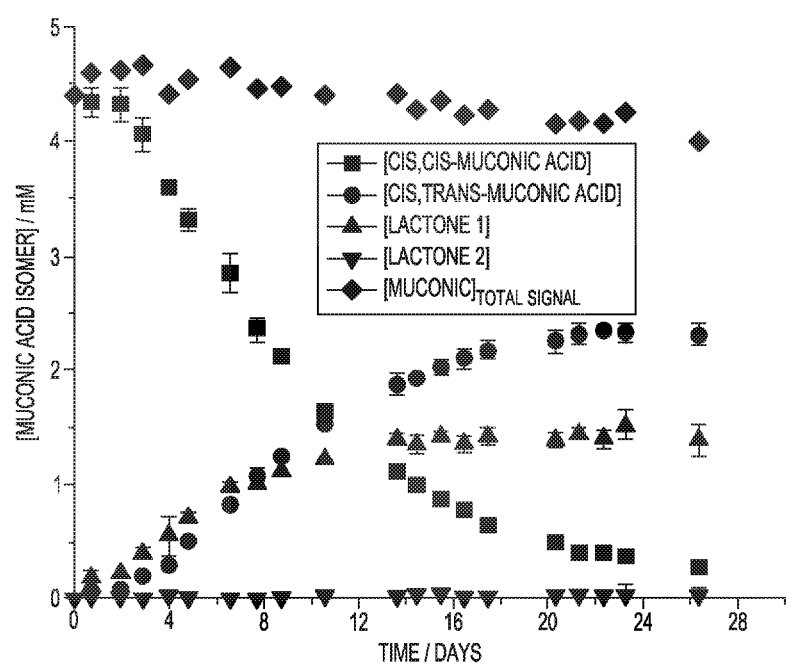
FIG. 7 illustrates the concentration of isomers and products when cis,cis-muconic acid was heated at 75° C. with $LaBr_3 \times 6H_2O$ at a pH of about 3 in $D_2O$ for 26 days, in accordance with various embodiments.
Figure 8:
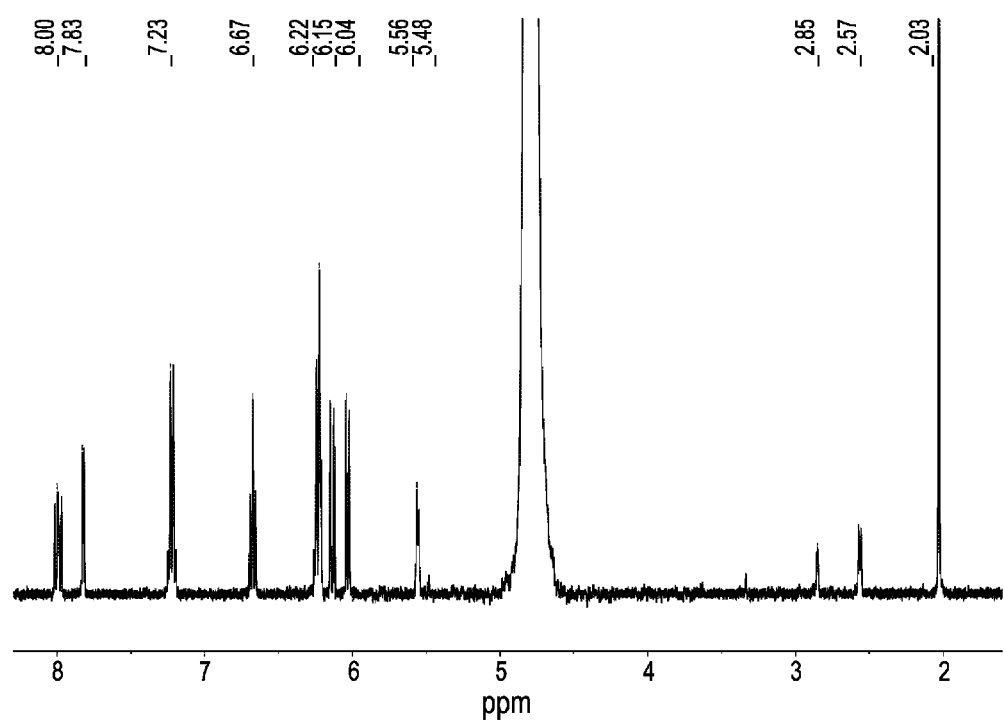
FIG. 8 illustrates a $^1H$ NMR of cis,cis-muconic acid that was heated for 10.6 days at 75° C. with $LaBr_3 \times 6H_2O$ at a pH of about 3 in $D_2O$, in accordance with various embodiments.

A stock solution containing 4.6 mM cis,cis-muconic acid and 1.3 mM acetic acid (internal standard) was prepared in $D_2O$. Solid Lanthanum(III)bromide hexahydrate (LaBr$_3$× 6H$_2$O) was added, and the resulting solution contained 230 mM La$^{3+}$ salts (pH ~3-4). This mixture was added to a J. Young NMR tube and heated at 75° C. for 3 weeks with NMR spectra acquired daily. FIG. 7 illustrates the concentration of isomers and products over time. FIG. 8 illustrates a $^1H$ NMR at 10.6 days.

Figure 9:
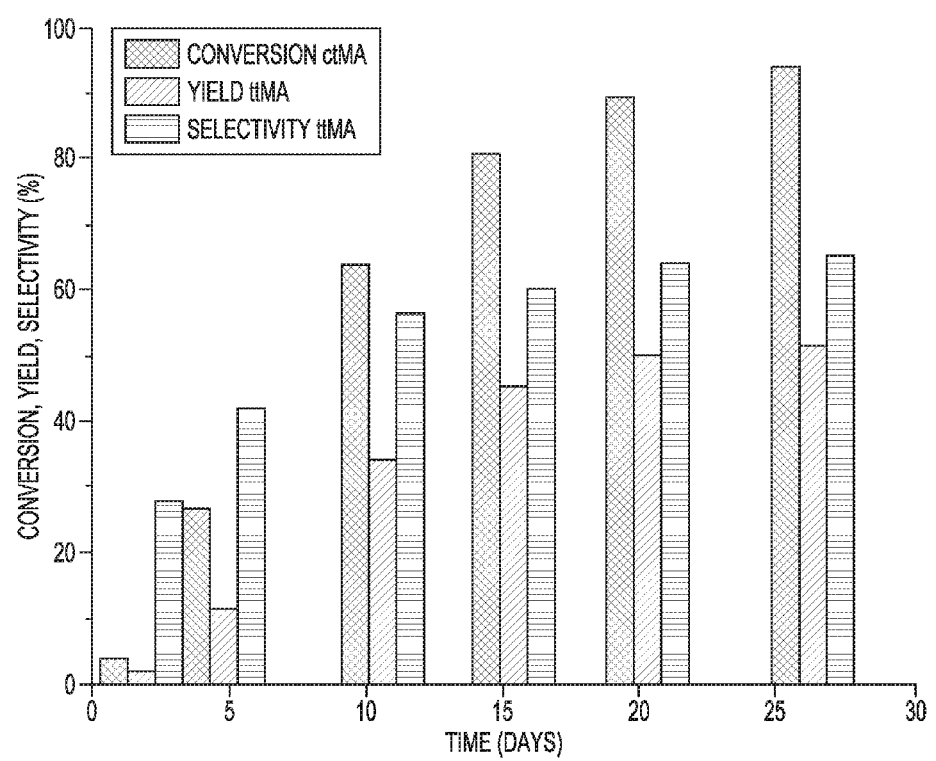
FIG. 9 illustrates the conversion of cis,trans-muconic acid, and the yield and selectivity toward trans,trans-muconic acid over time, in the presence of $LaBr_3 \times 6H_2O$ at a pH of about 3-4, in accordance with various embodiments

FIG. 9 illustrates the conversion of cis,trans-muconic acid, and the yield and selectivity toward trans,trans-muconic acid over time. At 22 days, the maximum yield of the trans,trans-muconic acid was 53%; the conversion of the cis,trans-muconic acid was 91%; and the selectivity toward the trans,trans-muconic acid was 58%.

La$_{aq}^{3+}$ has a high affinity for carboxylate. It is believed that the La$^{3+}$ coordinates with the carboxylate groups in the muconic acid, as shown in Scheme 6. The LaBr$_3$×6H$_2$O had a sensitivity to pH. When pH was too low, there were no carboxylate groups to bind (e.g., they were in the acid form). When pH was too high. La(H$_2$O)$_6^{3+}$ became La(OH)$_n$(H$_2$O)$_{6-n}$.

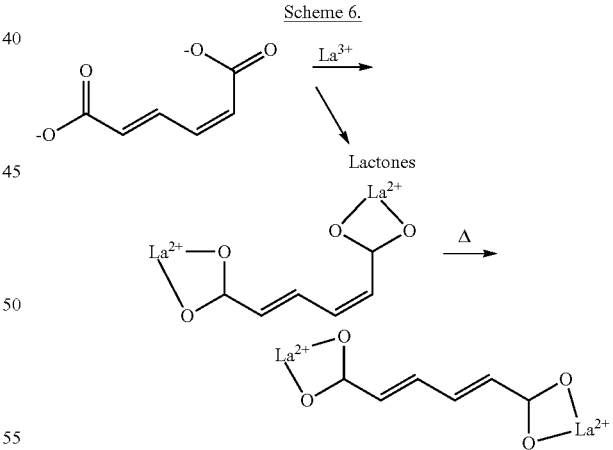

Scheme 6.

Example 2-2

Figure 10:
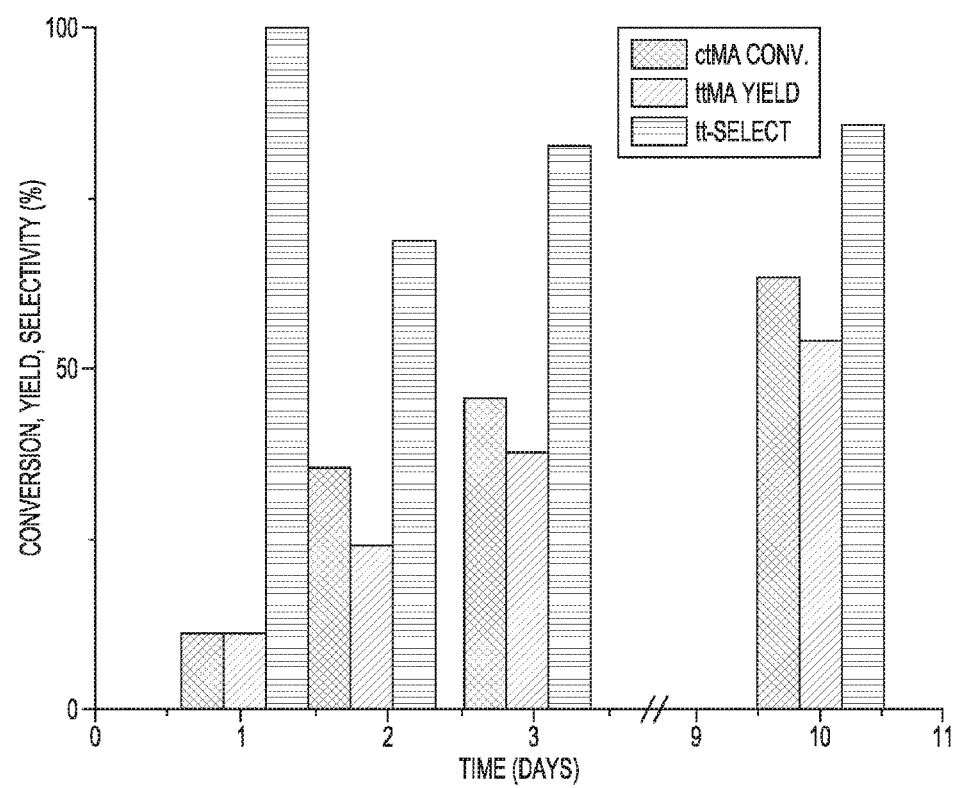
FIG. 10 illustrates the conversion of cis,trans-muconic acid, and the yield and selectivity toward trans,trans-muconic acid over time, in the presence of $LaBr_3 \times 6H_2O$ at a pH of about 5, in accordance with various embodiments.

Example 2-1 was followed, using a concentration of 4.5 mM cis,trans-muconic acid, with 298 mM of the LaBr$_3$× 6H$_2$O, at a pH of about 5, and with heating at 90° C. FIG. 10 illustrates the conversion of cis,trans-muconic acid, and the yield and selectivity toward trans,trans-muconic acid over time. At 10 days, the maximum yield of the trans,trans-muconic acid was 55%; the conversion of the cis,trans-muconic acid was 64%; and the selectivity toward the trans,trans-muconic acid was 85%.

Part 3. Aluminum Tribromide.

Example 3-1

Extra-dry $CD_3CN$ was obtained by standard solvent drying methods. Approximately 3 mg of cis,trans-muconic acid was massed in a dry box and added to a J. Young tube. Then 1.2 mg $AlBr_3$ (anhydrous) was added to the same NMR tube. Roughly 600 mL of extra dry $CD_3CN$ was added and the J. Young tube was sealed. The solution was then heated at 75° C. for 3 hours and $^1H$ NMR spectra was acquired throughout.

The $AlBr_3$ increased the selectivity of the reaction, leading to 40% yield of trans,trans-muconic acid within 3 h at 75° C. with 80% conversion of the cis,trans-muconic acid, and with 40% yield of the dilactone. It is believed that the Lewis acid weakened the C=C bonds and enabled the rotation along the C—C axis to form the thermodynamically favored trans,trans isomer.

A control sample was prepared without $AlBr_3$ and heated. This control sample produced only muconolactone. Addition of 2 mg $AlBr_3$ to the muconolactone solution resulted in formation of the dilactone species, as shown in Scheme 7.

muconic acid isomers exhibit a very high solubility in DMSO, which allowed performing a successful Diels-Alder reaction with the trans,trans-muconic acid without any separation or purification, allowing for an efficient and convenient one-pot isomerization/Diels-Alder reaction.

Example 4-2. DMSO at 75° C.

Figure 11:
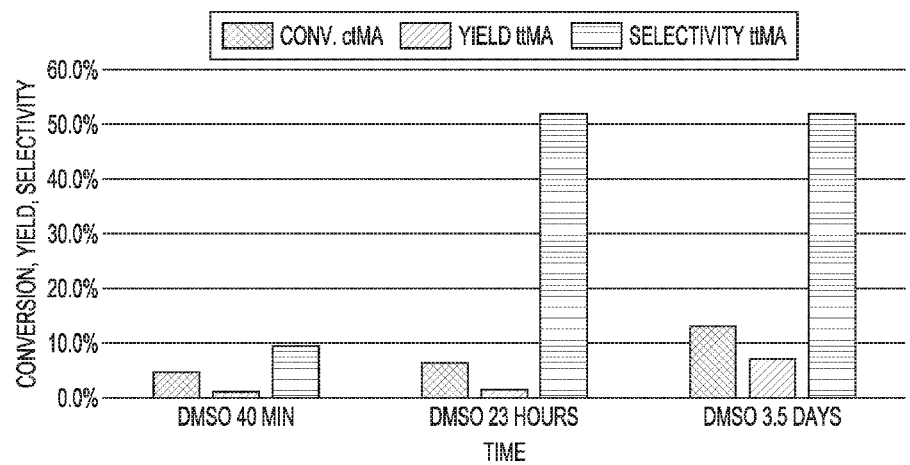
FIG. 11 illustrates the conversion of cis,trans-muconic acid, and the yield and selectivity for trans,trans-muconic acid, in DMSO at 75° C., in accordance with various embodiments

Example 4-1 was followed, with 4 mg of cis,trans-muconic acid in 0.5 mL DMSO, using a temperature of 75° C. Although the reaction proceeded more slowly than at 100° C., no degradation products were formed. FIG. 11 illustrates the conversion of cis,trans-muconic acid, and the yield and selectivity for trans,trans-muconic acid. After 3 days, the reaction was not monitored.

Example 4-3. DMSO at 75° C. with $AlBr_3$

Figure 12:
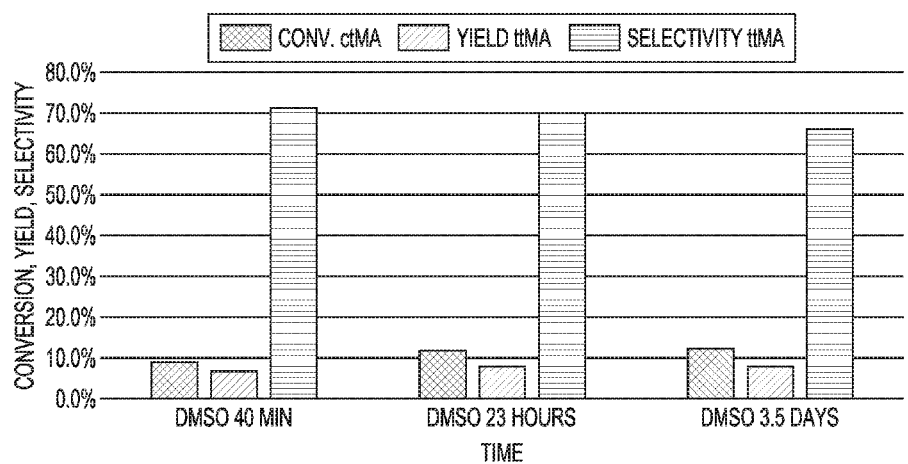
FIG. 12 illustrates the conversion of cis,trans-muconic acid, and the yield and selectivity for trans,trans-muconic acid, in DMSO with $AlBr_3$ at 75° C., in accordance with various embodiments.

Example 4-1 was followed, using 4 mg cis,trans-muconic acid in 5 mL DMSO, with 5 mg $AlBr_3$, at 75° C. The $AlBr_3$ catalyst reacted rapidly with DMSO and deactivates (smelled like thiols). Within milliseconds of addition to the reaction mixture the reaction had up to 8% yields of ttMA. FIG. 12 illustrates the conversion of cis,trans-muconic acid, and the yield and selectivity for trans,trans-muconic acid.

Scheme 7.

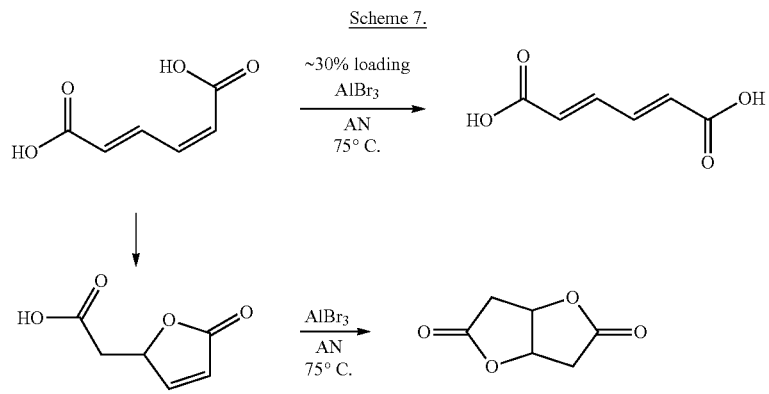

Part 4. Dimethylsulfoxide, Part I.

Example 4-1. DMSO at 100° C.

Figure 20:
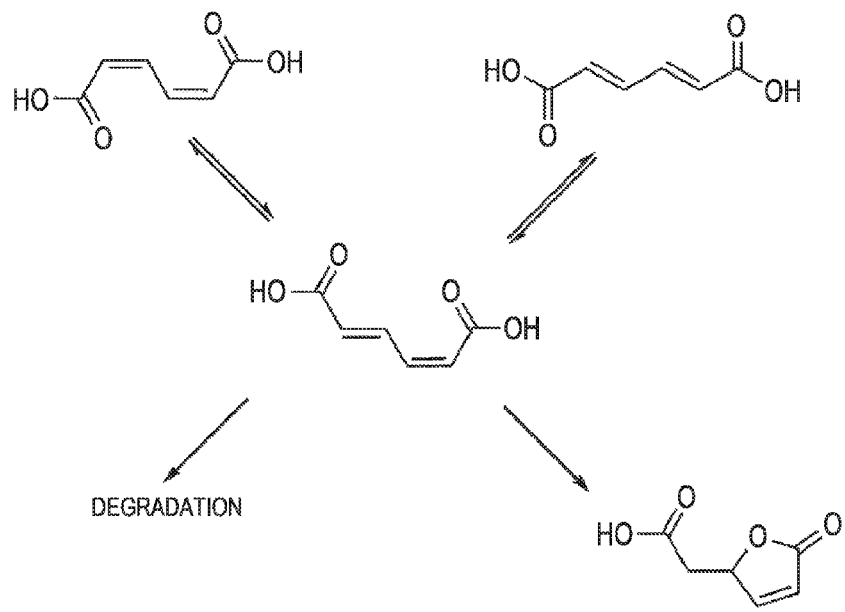
FIG. 20 illustrates a reaction scheme, in accordance with various embodiments.

A 9 mM solution of cis,trans-muconic acid was prepared in DMSO-d6, without any additional inorganic catalyst. This solution was added to a 5 mL glass reaction vessel with conical bottom and a 'V'-shaped stir bar. The reaction vial was placed in a 100° C. oil bath with stir rate of 600 rpm. The sample was removed from the oil bath at 19 hours and a $^1H$ NMR spectrum was acquired. The solution was then returned to the oil heating bath and was removed again after an additional 21 hours and $^1H$ NMR acquired again. The solution was added to the bath a third time, but prolonged heating resulted in decomposition. The isomerization is illustrated in FIG. 20.

After 40 h at 100° C. trans,trans-muconic acid was produced with 90% selectivity at 62% conversion (56% yield), with 6% yield of muconolactone, and with less than 1% unidentified decomposition products.

This discovery offers interesting perspectives as DMSO is a common solvent in industry. DMSO is cheap and presents a lower toxicity (LD50) than ethanol. In addition, the Part 5. Dimethyl Sulfoxide, Part II.

General.

Figure 14:
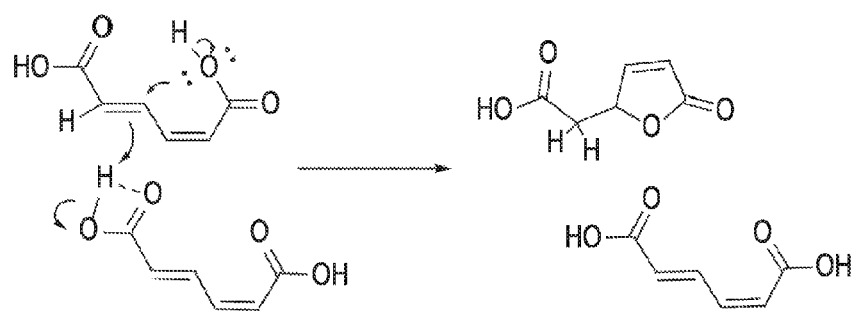
FIG. 14 illustrates a muconic acid-catalyzed lactonization scheme, in accordance with various embodiments.

Cis,cis-muconic acid (ccMA), trans,trans-muconic acid (ttMA). DMSO-d6 (99.96% D), and dimethyl sulfone ($DMSO_2$) were purchased from Sigma-Aldrich. Cis,trans-muconic acid (ctMA) was prepared by methods previously described in the literature. Extra-dry DMSO-d6 was refluxed over $CaH_2$ and stored over sieves. For experiments in which strict water-free conditions were required; a mother solution containing ctMA and $DMSO_2$ (internal standard) with dried DMSO-d6 was prepared in an inert atmosphere box. Experiments in which the effect of [MA] was investigated utilized 600 μL of the mother solution in J. Young tubes containing additional solid ctMA. ctMA concentrations were determined by NMR vs $DMSO_2$ internal standard in the mother solution. The tubes were sealed, placed in an Erlenmeyer flask with a thermometer, and heated in a laboratory oven. The experiment at 121° C. was heated in an aluminum heating block equipped with a thermocouple. Samples were removed from the oven, cooled to room temperature, and analyzed by $^1H$ NMR throughout the duration of the experiment. Experiments that investigated the effect of water were prepared in DMSO-d6 that had not been dried. Instead, aliquots of a mother solution containing ctMA and DMSO$_2$ added to J. Young tubes and H$_2$O was added via syringe (<1 μL-100 μL). The water concentration was determined by $^1$H NMR signal relative to DMSO$_2$ standard. High water concentration experiments (>1 M) utilized D$_2$O to minimize interference with $^1$H NMR spectra. D$_2$O was added to the mother solution with an electronic micropipette (>100 μL).

was observed to occur much more readily at elevated [MA]. The significant decrease in selectivity to ttMA with increasing [MA] helps explain the above described transformation at 300 g/L, and may suggest an acid catalyzed pathway for lactonization analogous to the aqueous system. However, in this particular system muconic acid is both the reactant and the catalyst as is shown in FIG. 14.

TABLE 1

Effect of initial ctMA concentration on observed rate constants at 87° C. and product selectivity at 20 and 50% conversion.

| [ctMA]$_o$ (mM) | $k_{obs}$ × 10$^6$ (s$^{-1}$)$^a$ | half-life (days) | Selectivity (20% Conversion) | | | | Selectivity (50% Conversion) | | | |
| --- | --- | --- | --- | --- | --- | --- | --- | --- | --- | --- |
| | | | ccMA | ttMA | Mlac | Lac2 | ccMA | ttMA | Mlac | Lac2 |
| 5.5 | 2.6 | 3.1 | 0.8% | 19.0% | 35.0% | 37.3% | 0.4% | 14.6% | 26.0% | 31.0% |
| 29.0 | 1.9 | 4.2 | 6.3% | 12.0% | 51.5% | 25.0% | 1.6% | 6.4% | 34.8% | 34.2% |
| 45.0 | 1.8 | 4.4 | 6.5% | 6.3% | 55.0% | 26.0% | 1.8% | 4.0% | 37.6% | 35.6% |
| 79.0 | 2.1 | 3.8 | 7.5% | 3.0% | 47.5% | 15.0% | 1.6% | 3.0% | 36.4% | 32.4% |

$^a k_{obs}$ was determined at low conversion (ca. 20%) from eq 1. Error in $k_{obs}$ was determined by least squares method to be ±1 × 10$^{-7}$ s$^{-1}$.

Dilution of [ctMA] was adjusted by addition of solid ctMA, and was again determined relative to [DMSO$_2$] internal standard. $^1$H NMR spectra were collected with a Bruker AVIII600 spectrometer, and spectra were analyzed with MestReNova software. Data were plotted with OriginPro 9.1 software.

Introduction.

The $^1$H NMR chemical shifts for ctMA indicate that the molecule is in its fully protonated state (e.g. ctMAH$_2$). Therefore, lactonization of ctMAH$^-$ ($k_{ctMAH-}$~10×$k_{ctMAH2}$) is not a concern in this system. Our previous results indicated that ttMA was the main product upon heating a solution of ccMA or ctMA in DMSO. Given the marked difference in solubilities of MA in aqueous solutions and DMSO, the conversion was investigated on a more industrially relevant scale. Therefore, a sample on the order of 300 g/L (~2M) was prepared in DMSO-d6. $^1$H NMR spectra at such high concentrations were qualitative at best. Heating a highly concentrated solution of ccMA to 100° C. overnight yielded primarily muconolactone (Mlac) with no indication of ttMA. Analysis of the spectra was hindered by the very broad signals, however, it is estimated that conversion was complete within this time period. This result was contrary to what was expected based on a preliminary solvent screening. We, therefore, decided to investigate this system kinetically in order to develop optimization strategies.

Example 5-1. Effect of Muconic Acid Concentration in Dry DMSO-d6

Figure 13:
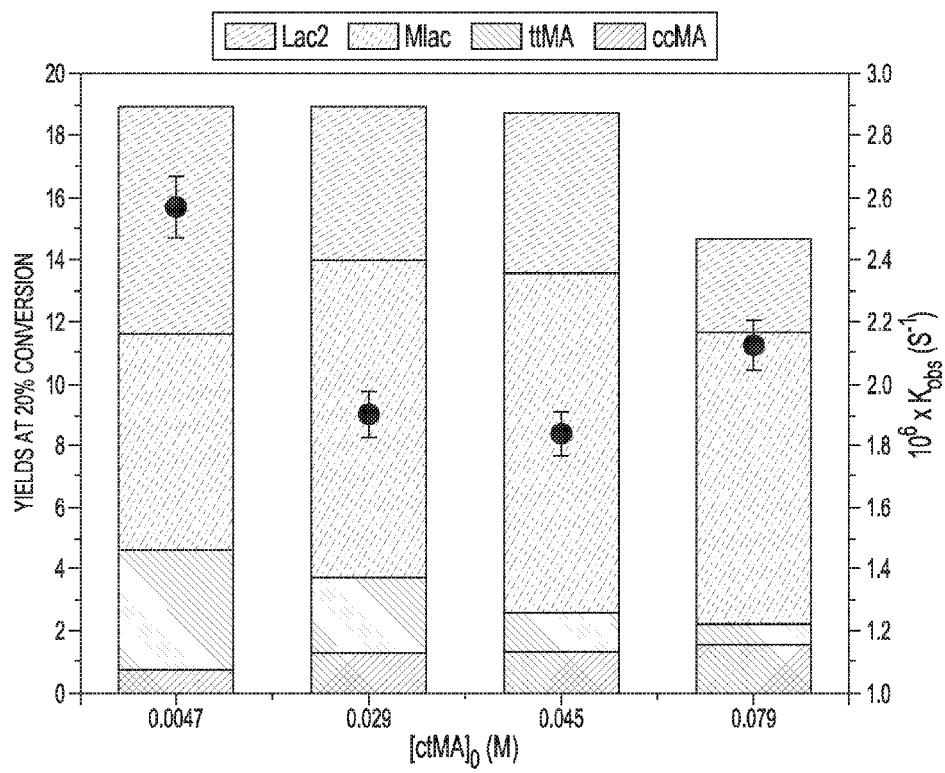
FIG. 13 illustrates yield and rate constants versus $[ctMA]_o$, in accordance with various embodiments.

The majority of the experiments in this Part contained 5-80 mM ctMA and were heated to 87° C. The maximum selectivity toward ttMA production was observed at the lowest concentrations of ctMA, and gradually decreased from 19% to 3% as [ctMA] was increased from 5 mM to 79 mM (Table 1 and FIG. 13). FIG. 13 illustrates the effect of [ctMA]$_o$ on yields at 20% conversion (left axis) and the observed rate constant (right axis). 5-80 mM ctMA solutions in DMSO-d6 and heated to 87° C. Kinetic traces and product distributions were obtained by $^1$H NMR monitoring with DMSO$_2$ internal standard. The ttMA selectivity of the 5 mM solution decreased to roughly 15% at 50% conversion. Several new signals were observed and have been attributed to MA degradation to unidentified products. The degradation Kinetic traces obtained for the consumption of ctMA fit first order rate equations (eq 1) for all [ctMA]. FIG. 13 shows the observed rate constants ($k_{obs}$) obtained from equation 1 plotted against [ctMA]$_o$, wherein equation 1 (eq 1) is ln([ctMA]$_t$/[ctMA]$_o$)=–$k_{obs}$×t+const., wherein [ctMA]$_t$=concentration of ctMA at time t, [ctMA]$_o$=initial concentration of ctMA, $k_{obs}$=observed first order rate constant, t=time in seconds, and conts.=a constant from integration of the first order rate law.

Example 5-2. Effect of Low Water Concentrations on Muconic Acid Isomerization

The effect of water on the reaction system was investigated. $^1$H NMR spectra of samples containing water (5 mM-744 mM) indicate the ctMAH$_2$ is the primary form under all conditions (e.g. MA is fully protonated just as in the absence of water).

Figure 15:
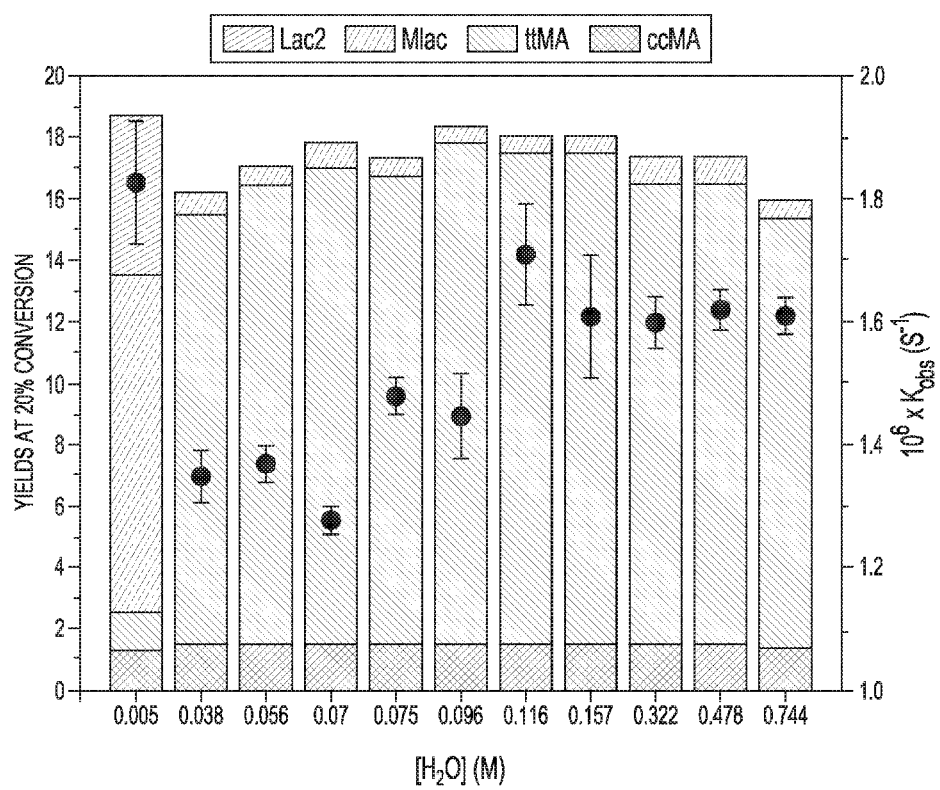
FIG. 15 illustrates yield and rate constant versus $[H_2O]$, according to various embodiments.
Figure 16:
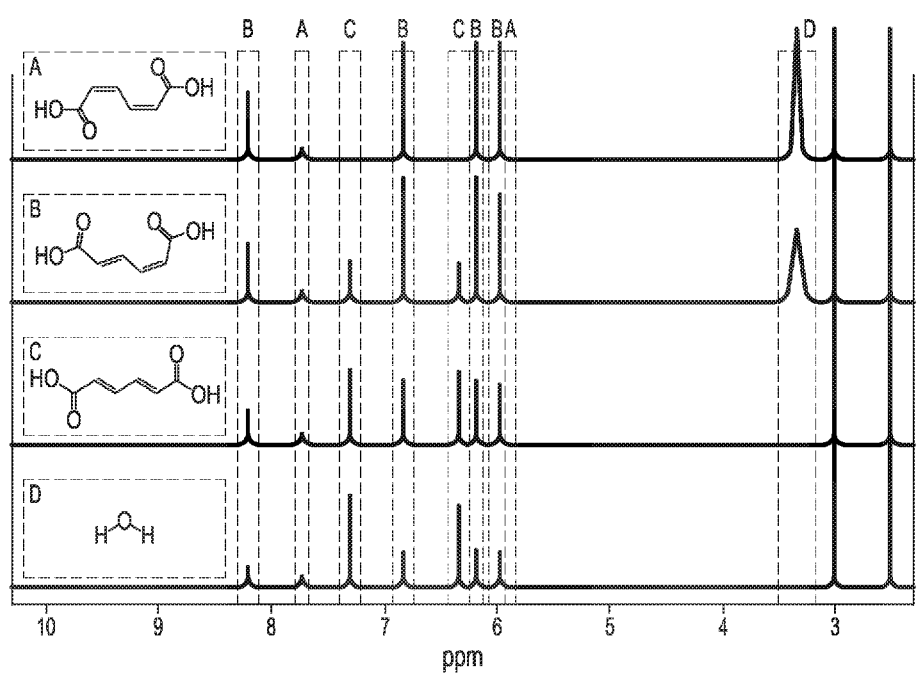
FIG. 16 illustrates $^1H$ NMR spectra showing conversion of ctMA in the presence of $H_2O$, according to various embodiments.

Table 2 illustrates the conditions and the resulting selectivities. At very low [H$_2$O] (H$_2$O:MA~1:10), the reactivity was similar to the dry DMSO system at 20% conversion (compare 45 mM ctMA in Table 1 with 48 mM ctMA and 5 mM H$_2$O in FIG. 15). FIG. 15 illustrates effect of water content on yields at 20% conversion (left axis) and the observed rate constant (right axis). Microliter amounts water were added to 600 μl of 48.0 mM ctMA solutions in DMSO-d6 and heated to 87° C. Kinetic traces and product distributions were obtained by $^1$H NMR monitoring with DMSO$_2$ internal standard. The improvement in selectivity to ttMA is dramatic at 96 mM H$_2$O (H$_2$O:MA~2:1) as it increased 13-fold to 81.5% (88% if conversion is considered as Conv.=[ctMA]$_o$–([ctMA]$_t$+[ccMA]$_t$)/[ctMA]$_o$ due to the relatively rapid ccMA⇌ctMA equilibrium). High selectivity to ttMA (82%) was maintained up to 50% conversion, but at 72% conversion the selectivity decreased to 73%. FIG. 16 illustrates $^1$H NMR (600 MHz, DMSO-d6) spectra of 48 mM ctMA+96 mM H$_2$O heated to 87° C. at 0 (top), 18.5, 52, and 72.5% (bottom) conversion. Throughout the reaction the $^1$H NMR signal of H$_2$O (3.34 ppm) gradually decreased as shown in FIG. 16 until it was not observable at ca. 60% conversion in the 96 mM H$_2$O sample. The samples containing 38 and 56 mM H$_2$O show a minor decrease in selectivity to ttMA from 20% to 50% conversion. The selectivity to ttMA in all other samples increases as the H$_2$O signal decreases, suggesting that an optimal ratio of H$_2$O:

MA exists for highly selective production of ttMA (>75%). The optimal range for which appears to be quite broad: $H_2O$:MA between 0.9:1 and 10:1. No apparent trend was observed for lactonziation at low [$H_2O$].

out with a $D_2O$:MA of 1.9-2.6:1. Under these conditions the majority of the water is expected to interact primarily with the carboxyl moieties thus lowering the apparent acidity and minimizing the acid catalyzed lactonization shown in FIG.

TABLE 2

Effect of water concentration on muconic acid isomerization in DMSO[a].

| [$H_2O$]$_o$ (mM) | $10^6 \times$ k$_{obs}$ (s$^{-1}$) | half-life (days) | Selectivity at 20% Conversion | | | Selectivity at 50% Conversion | | |
|---|---|---|---|---|---|---|---|---|
| | | | ccMA | ttMA | Mlac | ccMA | ttMA | Mlac |
| 5.0 | 1.8 | 4.5 | 6.5% | 6.3% | 55.0% | 1.8% | 4.0% | 37.6% |
| 37.7 | 1.4 | 5.9 | 7.5% | 70.0% | 3.5% | 1.8% | 69.8% | 2.8% |
| 55.6 | 1.4 | 5.9 | 7.5% | 75.0% | 3.0% | 1.8% | 71.2% | 2.8% |
| 70.1 | 1.3 | 6.2 | 7.5% | 77.5% | 4.0% | 1.9% | 79.0% | 2.7% |
| 74.6 | 1.5 | 5.4 | 7.5% | 76.0% | 3.0% | 1.8% | 78.2% | 2.6% |
| 96.1 | 1.5 | 5.5 | 7.5% | 81.5% | 3.0% | 1.8% | 82.0% | 2.6% |
| 115.8 | 1.7 | 4.7 | 7.5% | 80.0% | 2.5% | 1.8% | 70.0% | 2.4% |
| 157.4 | 1.6 | 5.0 | 7.5% | 80.0% | 2.5% | 1.8% | 72.0% | 2.2% |
| 322.0 | 1.6 | 5.0 | 7.5% | 75.0% | 4.5% | 2.1% | 83.7% | 2.5% |
| 478.0 | 1.6 | 5.0 | 7.5% | 75.0% | 4.5% | 2.4% | 85.7% | 2.4% |
| 744.0 | 1.6 | 5.0 | 7.0% | 70.0% | 3.0% | 2.4% | 79.0% | 2.4% |

[a]Selectivities at 20 and 50% conversion for 48 mM ctMA in DMSO-d6 with varying concentrations of water at 90° C.
[b]k$_{obs}$ acquired from fits to eq 1 at 20% ctMA conversion.
[c]5 mM $H_2O$ sample also contains Lac2.

Kinetically, the conversion of ctMA behaves similarly to the system described above in that the traces fit first order rate equations. As the water content increases there is an initial ~20% drop in k$_{obs}$ between 5 mM and 38 mM followed by a gradual increase (70-120 mM $H_2O$) and a plateau from 120 mM and 744 mM. The initial decrease was expected under the assumption that an acid catalyzed lactonization pathway exists, and that introduction of water to the system would decrease the apparent pKa. The sigmoidal shape observed in FIG. 15 could be indicative of a ctMA-2$H_2O$ complex that is roughly 20% more active for isomerization to ttMA than a ctMA-$H_2O$ complex. The plateau achieved at the highest [$H_2O$] coupled with decreasing $H_2O$ signal and steady decline in ttMA selectivity above 160 mM $H_2O$ could be indicative of $H_2O$ being a potential reactant in the degradation pathway.

Example 5-3. Kinetic Isotope Effects at Low Water Concentration

Figure 17:
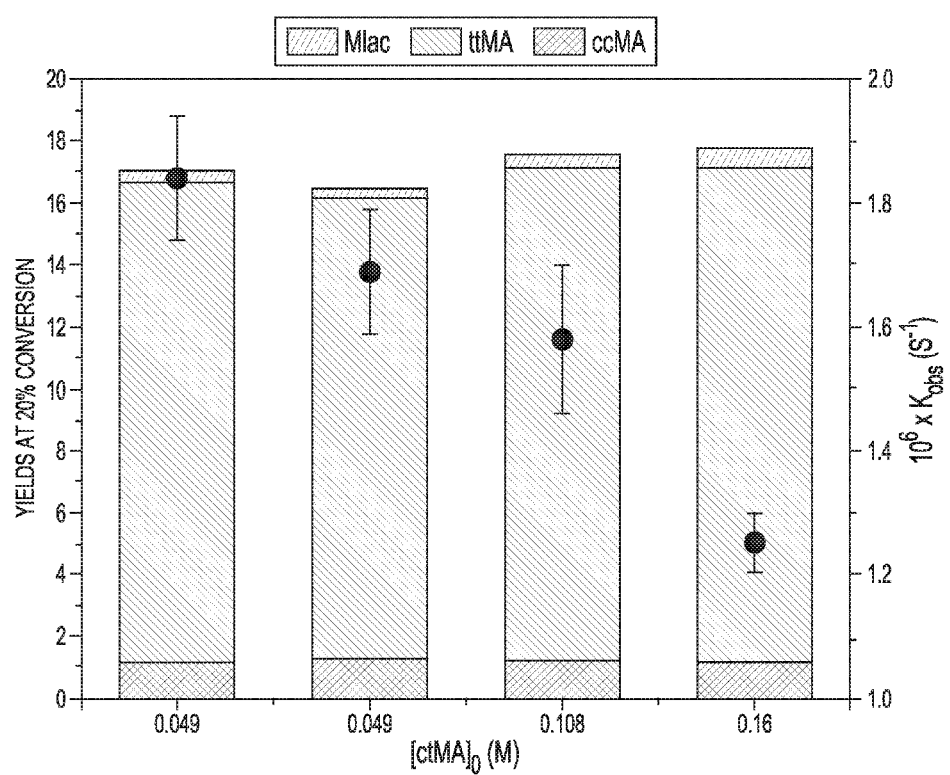
FIG. 17 illustrates yield and rate constant versus $[ctMA]_o$, in accordance with various embodiments.

Solutions containing 50 mM ctMA and 126 mM $H_2O$ and $D_2O$ were heated to 87° C. for several days. Kinetic traces obtained by monitoring ctMA consumption yielded similar k$_{obs}$ (1.84 and 1.7×10$^{-6}$ s$^{-1}$, respectively). Likewise, ttMA yields at 20% conversion were nearly identical, however, the yield of Mlac was three times higher in $H_2O$ than $D_2O$ (0.3% vs. 0.1%, respectively shown in FIG. 17). FIG. 17 illustrates the effect of [ctMA]$_o$ with 2-2.6 equivalents of $H_2O$ (column 1) and $D_2O$ (columns 2-4) on yields at 20% conversion (left axis) and the observed rate constant (right axis) for ctMA solutions in DMSO-d6 heated to 87° C. Kinetic traces and product distributions were obtained by $^1$H NMR monitoring with DMSO$_2$ internal standard. This apparently minute difference in yield is indicative of water involvement in the lactonization process. At low [$H_2O$] this is negligible, as such it was not observed in k$_{obs}$ for ctMA consumption. However, the effect of high [$H_2O$] has a significant effect on lactonization, vide infra.

Example 5-4. Effects of Muconic Acid Concentration at Low Water Concentration

To probe the effect of [ctMA]$_o$ on the kinetics and yields at low water concentration these experiments were carried out with a $D_2O$:MA of 1.9-2.6:1. Under these conditions the majority of the water is expected to interact primarily with the carboxyl moieties thus lowering the apparent acidity and minimizing the acid catalyzed lactonization shown in FIG. 14. This assumption is supported by NOESY NMR experiments that indicate close proximity between the carboxyl moieties and $H_2O$ in the system as opposed to internal carbon atoms. The selectivity to cc- and ttMA at 20% conversion remained relatively constant between 50 and 160 mM ctMA (ca. 6 and 75-80%, respectively), but selectivity to Mlac increased 6-fold (FIG. 17). Additionally, k$_{obs}$ for ctMA consumption decreased with increasing [ctMA]$_o$ similar to the absence of water, however, unlike the trend observed in FIG. 13 the rate constants did not increase again at higher [ctMA]$_o$. This observation supports the non-reactive dimer hypothesis presented above.

Example 5-6. Effect of High Water Concentrations on Muconic Acid Isomerization

Figure 18:
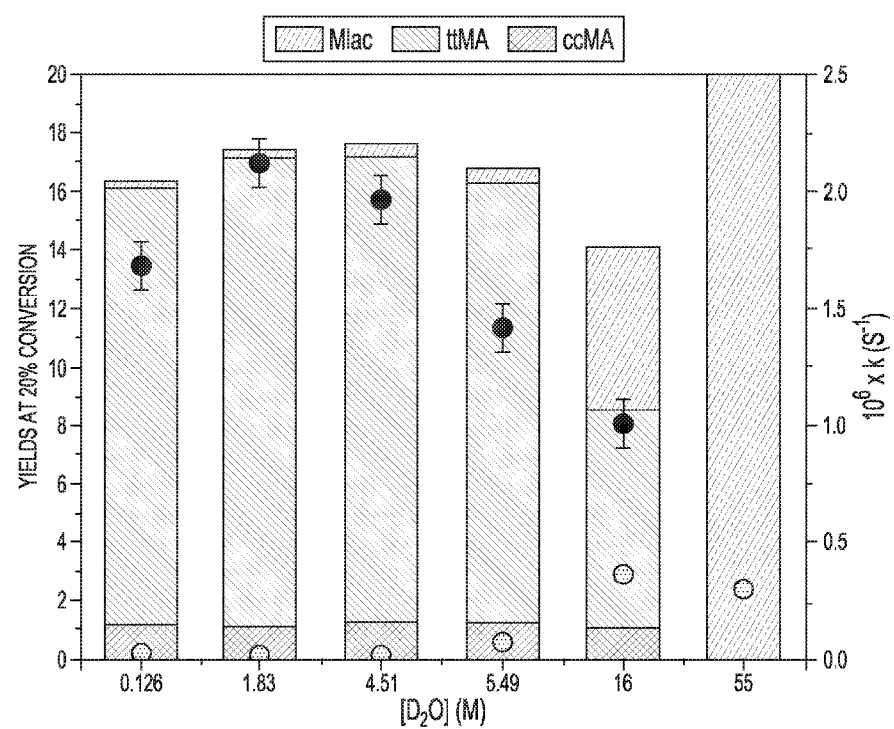
FIG. 18 illustrates yield and rate constant versus $[D_2O]$, in accordance with various embodiments.
Figure 19:
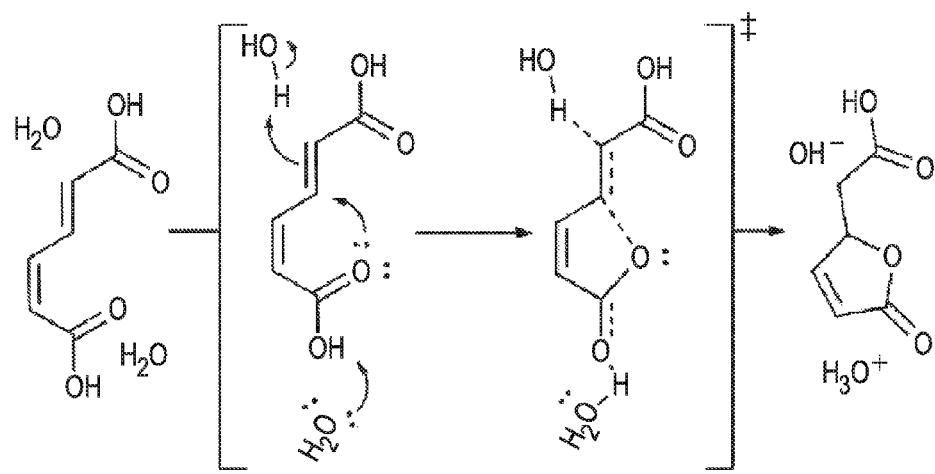
FIG. 19 illustrates a reaction scheme, in accordance with various embodiments.

The addition of $D_2O$ from 1.8 M-16.0 M to a 50 mM ctMA solution results in a decrease in k$_{obs}$ for ctMA consumption from 2.1-1.0×10$^{-6}$ s$^{-1}$ as shown in FIG. 18. FIG. 18 illustrates effect of high water content on yields at 20% conversion (left axis) and the observed rate constant for ctMA conversion (black dots, right axis) were obtained from equation 1 and observed rate constant for Mlac formation (grey dots, right axis) were estimated from equation 2. ca. 50 mM ctMA solutions in DMSO-d6+$D_2O$ were heated to 87° C. Kinetic traces and product distributions were obtained by $^1$H NMR monitoring with DMSO$_2$ internal standard. The column at 55 M $D_2O$ is from a previous experiment and the rate constant obtained is from simulations fit to experimental data in an aqueous system. ttMA yields at 20% conversion are relatively constant (15±1%) up to 8.5 M $D_2O$, but fall dramatically to 7.5% at 16 M $D_2O$. This was accompanied by a slight decrease in equilibrium concentrations of ccMA and a clear increase in Mlac yields. FIG. 18. There was a steady rise in Mlac yields from 1.8-8.5 M $D_2O$ from 0.1%-0.5% followed by a jump to 5.5% in 16 M $D_2O$. The isotope effect on Mlac yields can be extrapolated to nearly 17% Mlac yields (85% selectivity) at 16 M $H_2O$ at the cost of ttMA. Rate constants obtained by initial rates analysis for Mlac formation (eq 2) were plotted as a function of [$D_2O$] and suggest a ternary reaction in which water promotes lactonization through a push-pull type interaction in which one water molecule donates a proton to the carbon 5 to the cis-carboxylic acid while another accepts the proton from the cis-carboxylic acid. FIG. 19. This observation is consistent with the large negative entropy of activation ($\Delta S^{\ddagger}=-110$ j(molK)$^{-1}$) obtained from simulations fitted to experimental data for the same reaction in an aqueous system. The rate constant for Mlac formation at 16 M D$_2$O obtained from eq 2 is consistent with the aqueous simulations ($3.6 \pm 0.6 \times 10^{-7}$ s$^{-1}$ at 16 M D$_2$O and $3 \times 10^{-7}$ s$^{-1}$ at 55 M). This of course is only consistent if the reaction reaches saturation near 16 M D$_2$O (i.e. D$_2$O:ctMA=320:1). The elementary rate constant for the ternary reaction shown in FIG. 19 was calculated to be $1.2 \pm 0.2 \times 10^{-9}$ M$^{-2}$ s$^{-1}$.

Equation 2 is Rate$_{Mlac}$=[Mlac]$_t$/→k$_{Mlac}$= Rate$_{Mlac}$\{½([ctMA]$_o$-[ctMA]$_t$)\}, wherein [Mlac]$_t$=Mlac concentration at time t, t=time in seconds at which ~5% ctMA conversion was achieved, [ctMA]$_o$=initial ctMA concentration, and [ctMA]$_t$=concentration of ctMA at time t.

In addition to the solvent driven lactonization, higher water content also clearly shows a decrease in the rate constant for the parallel unimolecular formation of ttMA. The rate constant k$_{ttMA}$ was obtained by the same method as km, shown in equation 2. These rate constants were relatively constant up to 8.5 M D$_2$O, but were found to decrease by nearly a factor of 5 at 16 M D$_2$O. At 16 M D$_2$O k$_{ttMA}$ was roughly equivalent to k$_{Mlac}$, whereas at 8.5 M D$_2$O k$_{ttMA}$=84×k$_{Mlac}$. The exact driving forces behind the significant decrease in k$_{ttMA}$ are unclear. It, therefore, seemed prudent to test the reaction from the perspective of ttMA in attempt to identify if water has an effect on the ctMA⇌ttMA equilibrium observed at higher temperature, vide infra. Heating solutions of 50 mM ttMA in the presence of 1.8 and 16 M D$_2$O confirmed the existence of a ct- to ttMA equilibrium at 87° C. Comparison of k$_{obs}$ starting from both ctMA and ttMA yielded equilibrium constants that vary with [D$_2$O], K=8.1 and 4 at 1.78 M and 16 M D$_2$O, respectively. The observed rate constant for formation of ttMA decreases from $1.9 \times 10^{-6}$ s$^{-1}$ at 1.8 M D2O to $3.9 \times 10^{-7}$ s$^{-1}$ at 16 M D$_2$O. The observed rate constant for the reverse reaction is unaffected by [D$_2$O] at $3.6 \times 10^{-7}$ s$^{-1}$.

However, the solvent driven lactonization at high water concentration in conjunction with the significant decrease in k$_{ttMA}$ at a relatively modest 16 M D$_2$O (neat D$_2$O=55 M) explain why ttMA is never observed in an aqueous system in the absence of catalyst like $_{aq}$La$^{3+}$.

Example 5-7. Effects of Temperature & Kinetic Simulations

An investigation into the effects of temperature on isomerization and lactonization was carried out in the presence of ca. 2 equivalents of water in order to minimize solvent driven lactonization while promoting isomerization to ttMA. The product yields at 20% conversion and k$_{obs}$ for ctMA conversion are shown in FIG. 18. Selectivity to ttMA was relatively high for all three temperatures; 88, 80, and 88% at 60, 87, and 121° C., respectively (91, 88, and 93% considering ccMA⇌ctMA equilibrium). The reaction at 121° C. was fast enough (t$_{1/2}$=5.2 weeks, 5.2 days, and 1.7 hours at 60, 87, and 121° C., respectively) so that we were able to achieve equilibrium between ctMA and ttMA. To probe the temperature effects further kinetic simulations were run with KINSIM in accordance with the simplified reaction scheme shown in FIG. 20. Estimates for elementary rate constants were input based on the experimental values obtained from treatment of the data with either equation 1 or equation 2 above. The rate constants were finely tuned until simulated kinetic traces matched experimental ones for all species; including the loss of signal due to degradation from ctMA. The equilibrium constants, rate constants, and activation parameters are shown in Table 3.

TABLE 3

Equilibrium constants, rate constants, and activation parameters for the reactions outlined in FIG. 20.

| | Temperature (° C.) | | | Activation Parameters | |
|---|---|---|---|---|---|
| Reaction | 60 | 87 | 121 | $\Delta H^{\ddagger}$ kJ mol$^{-1}$ | $\Delta S^{\ddagger}$ J (molK)$^{-1}$ |
| K$_{cc\text{-}ct}$ | 68 | 55 | 50 | — | — |
| K$_{ct\text{-}tt}$ | 1.7 | 2.4 | 4.7 | — | — |
| k$_{ct \to tt}$ | $2.5 \times 10^{-7}$ | $1.2 \times 10^{-6}$ | $1.4 \times 10^{-4}$ | 110 ± 31 | −44 ± 85 |
| k$_{tt \to ct}$ | $1.5 \times 10^{-7}$ | $5.0 \times 10^{-7}$ | $3.0 \times 10^{-5}$ | 92 ± 28 | −103 ± 78 |
| k$_{ct \to Mlac}$ | $4.0 \times 10^{-9}$ | $3.1 \times 10^{-8}$ | $6.0 \times 10^{-6}$ | 128 ± 31 | −25 ± 86 |
| k$_{ct \to deg}$ | $2.0 \times 10^{-8}$ | $3.5 \times 10^{-7}$ | $3.0 \times 10^{-5}$ | 128 ± 14 | −11 ± 39 |

Example 5-8. Preparation of Bio-Advantaged Materials

The monomers cyclohex-1-ene-1,4-dicarboxylic acid (CH1DA) and cyclohex-2-ene-1,4-dicarboxylic acid (CH2DA) (FIGS. 4a and 4b, respectively) can be prepared by Diels-Alder cycloaddition of ethylene to ttMA. CH2DA is the initial product, but readily isomerizes to CH1DA likely due to the stabilization resulting from conjugation. At elevated temperatures (T≥180° C.) only CH1DA was observed in most solvents. A mixture of CH2DA and CH1DA could be obtained when Diels-Alder was carried out at 120° C. for 3 days, however, conversion was not complete within this time period and CH1DA was still the major product. Additionally. CH2DA is relatively stable in an acidic aqueous solution, but isomerizes readily to CH1 DA under basic conditions. Therefore, two approaches were employed to produce CH2DA with good purity and yield. Esterification of ttMA prior to Diels-Alder yielded the CH2DA dimethyl ester in 93% yield (6% CH1DA dimethyl ester) after 8 hours at 180° C.

Polyamides containing CH1 or 2DA and hexamethylenediamine (HMDA) were prepared as described for 3-hexenedioic acid (HDA)/HMDA polyamides reported earlier. The CH1DA/HMDA material exhibits a melting point of 123° C. (ca. 60° C. higher than HDA/HMDA). Like HDA/HMDA polyamides these materials are expected to allow for additional enhancement of the materials' properties through functionalization of the double bond, as described in U.S. Patent Application No. 62/253,485, filed Nov. 10, 2015, hereby incorporated in its entirety as if reproduced herein.

Example 5-9. Additional Experiments

Table 4 illustrates yield and selectivity for isomerization of ctMA in the presence of various amounts of water or D$_2$O at various temperatures. In one example, a solution of cis,trans-muconic acid heated to 121° C. provided ttMA in 73% yield with 85% selectivity within 8 hours.

TABLE 4

| Entry | H$_2$O:ctMA | Temp (° C.) | Reaction Time (days) | Maximum ttMA Yield | ttMA Selectivity |
|---|---|---|---|---|---|
| 1 | 0.8 | 87 | 13.4 | 50.0% | 71.3% |
| 2 | 1.1 | 87 | 13.4 | 51.5% | 72.1% |
| 3 | 1.5 | 87 | 13.7 | 51.4% | 68.6% |
| 4 | 1.5 | 87 | 13.4 | 51.1% | 70.2% |
| 5 | 2.0 | 87 | 13.4 | 52.8% | 64.1% |
| 6 | 2.5 | 87 | 7.5 | 50.9% | 78.4% |
| 7 | 2.6 | 87 | 7.5 | 45.9% | 71.8% |
| 8 | 3.2 | 87 | 13.4 | 51.4% | 68.4% |
| 9 | 6.4 | 87 | 13.7 | 57.0% | 70.3% |
| 10 | 9.6 | 87 | 13.7 | 61.9% | 76.5% |
| 11 | 14.3 | 87 | 13.7 | 55.5% | 68.1% |
| 12 (D$_2$O) | 40.7 | 87 | 7.5 | 55.9% | 77.6% |
| 13 (D$_2$O) | 102.5 | 87 | 7.5 | 51.7% | 73.1% |
| 14 (D$_2$O) | 202.1 | 87 | 7.0 | 43.4% | 72.5% |
| 15 (D$_2$O) | 320.8 | 87 | 8.7 | 10.8% | 24.3% |
| 16 | 2.8 | 60 | 52.1 | 51.1% | 95.7% |
| 17 | 3.4 | 121 | 0.3 | 72.6% | 84.4% |

Example 5-10. Diels-Alder Reactions

At low temperature (120° C. for 3 days) Diels-Alder cycloaddition of ethylene with trans,trans-muconic acid yielded a mixture of cyclohex-1-ene-1,4-diocarboxylic (~70%) and cyclohex-2-ene-1,4-dicarboxylic (~30%) acids due to the ready isomerization from cylcohex-2-ene to cyclohex-1-ene diacids. However, Diels-Alder cycloaddition (75% conversion after 8 hours at 180° C.) in dioxane solvent was 100% selective to cyclohex-2-ene-1,4-dicarboxylic acid without isomerization to cyclohex-1-ene-1,4-dicarboxylic acid. At elevated temperatures or in gamma-valerolactone, cyclohex-1-ene-1,4-dicarboxylic acid was exclusively obtained as a precipitate.

Example 5-11. Diels-Alder Reactions Using Esterified Starting Material

Esterification of trans, trans-muconic acid prior to cycloaddition of ethylene stabilizes the cyclohex-2-ene-1,4-dimethyl ester yielding 93% of the 2 isomer and 7% of the 1 isomer at conversions >99% after 8 hours at 200° C. The choice of solvent becomes inconsequential for Diels-Alder reactions with muconic esters due to an inability to deprotonate and form more stable resonance structures. Furthermore, esterification with a diol prior to cycloaddition is expected to eliminate the need for prepolymerization when preparing polyesters.

Example 5-12. Polyamide

A polyamide was prepared from cyclohex-1-ene-1,4-dicarboxylic acid and hexamethylenediamine by heating a physical mixture in an inert atmosphere to 200° C. for 30 minutes. The resulting materials had a melting point of 123-130° C. (~60° C. higher than that observed with 3-hexenedioic acid and hexamethylenediamine).

The terms and expressions that have been employed are used as terms of description and not of limitation, and there is no intention in the use of such terms and expressions of excluding any equivalents of the features shown and described or portions thereof, but it is recognized that various modifications are possible within the scope of the embodiments of the present invention. Thus, it should be understood that although the present invention has been specifically disclosed by specific embodiments and optional features, modification and variation of the concepts herein disclosed may be resorted to by those of ordinary skill in the art, and that such modifications and variations are considered to be within the scope of embodiments of the present invention.

ADDITIONAL EMBODIMENTS

The following exemplary embodiments are provided, the numbering of which is not to be construed as designating levels of importance:

Embodiment 1 provides a method of forming trans,trans-muconic acid, the method comprising:

heating a starting material composition to form a product composition comprising trans,trans-muconic acid, wherein the starting material composition comprises cis,cis-muconic acid, cis,trans-muconic acid, or a combination thereof, and an electrophilic compound, an organic solvent, or a combination thereof.

Embodiment 2 provides the method of Embodiment 1, wherein the starting material composition comprises the cis,cis-muconic acid and is substantially free of cis,trans-muconic acid.

Embodiment 3 provides the method of any one of Embodiments 1-2, wherein the starting material composition comprises the cis,trans-muconic acid and is substantially free of cis,cis-muconic acid.

Embodiment 4 provides the method of any one of Embodiments 1-3, wherein the heating the starting material to form the product composition is free of electrochemical reactions.

Embodiment 5 provides the method of any one of Embodiments 1-4, wherein the starting material composition is an aqueous starting material composition.

Embodiment 6 provides the method of any one of Embodiments 1-5, wherein the starting material composition comprises an organic solvent that is a polar aprotic solvent.

Embodiment 7 provides the method of any one of Embodiments 1-6, wherein the organic solvent comprises dimethylsulfoxide (DMSO), acetonitrile (CH$_3$CN), tetrahydrofuran (THF), ethyl acetate (EtOAc), dimethylformamide (DMF), γ-valerolactone (GVL), methanol, ethanol, 2-propanol, hexanol, toluene, or a combination thereof.

Embodiment 8 provides the method of any one of Embodiments 1-7, wherein the organic solvent is dimethylsulfoxide (DMSO).

Embodiment 9 provides the method of any one of Embodiments 1-8, wherein the starting material composition further comprises water, D$_2$O, or a combination thereof.

Embodiment 10 provides the method of Embodiment 9, wherein the starting material composition is substantially free of solvents other than DMSO and the water and the D$_2$O.

Embodiment 11 provides the method of any one of Embodiments 1-10, wherein about 0.000001 wt % to about 20 wt % of the starting material composition is water, D$_2$O, or a combination thereof.

Embodiment 12 provides the method of any one of Embodiments 1-11, wherein about 0.00001 to about 2 wt % of the starting material composition is water, D$_2$O, or a combination thereof.

Embodiment 13 provides the method of any one of Embodiments 1-12, wherein the starting material composition is about 1 to about 20 molar equivalents of water, D$_2$O, or a combination thereof relative to total moles of cis,cis-muconic acid and cis,trans-muconic acid.

Embodiment 14 provides the method of any one of Embodiments 1-13, wherein the starting material composition is about 3 to about 10 molar equivalents of water. $D_2O$, or a combination thereof relative to total moles of cis,cis-muconic acid and cis,trans-muconic acid.

Embodiment 15 provides the method of any one of Embodiments 1-14, wherein the concentration of the cis,cis-muconic acid and the cis,trans-muconic acid in the starting material composition is about 0.000001 g/L to about 350 g/L.

Embodiment 16 provides the method of any one of Embodiments 1-15, wherein the concentration of the cis,cis-muconic acid and the cis,trans-muconic acid in the starting material composition is about 0.1 g/L to about 300 g/L.

Embodiment 17 provides the method of any one of Embodiments 1-16, wherein the starting material composition is substantially free of the electrophilic compound.

Embodiment 18 provides the method of any one of Embodiments 1-17, wherein the electrophilic compound is a Lewis acid.

Embodiment 19 provides the method of Embodiment 18, wherein the Lewis acid comprises $Li^+$, $Na^+$, $K^+$, $BeMe_2$, $Be^{2+}$, RMgX, $Mg^{2+}$, $Ca^{2+}$, $Sr^{2+}$, $AlCl_3$, $AlMe_3$, $AlH_3$, $Al(OR)_3$, $Al^{3+}$, $GaMe_3$, $InMe_3$, $In^{3+}$, $SnR_3^+$, $SnMe_2^{2+}$, $Sn^{2+}$, $Sc^{3+}$, $La^{3+}$, $Ti(OR)_4$, $Ti^{4+}$, $Zr^{4+}$, $VO_2^+$, $Cr^{3+}$, $Fe^{3+}$, $Co^{3+}$, $Ir^{3+}$, $Th^{4+}$, $UO_2^{2+}$, $Pu^{4+}$, $Yb^{3+}$, $GaH_3$, $Sn(OR)_4$, $SnCl_4$, $Pb^{2+}$, $Sb^{2+}$, $Bi^{3+}$, $Sc(OTf)_3$, $ScCl_3$, $Fe^{2+}$, $Co^{2+}$, $Ni^{2+}$, $Cu^{2+}$, $RZn^+$, $Zn^{2+}$, $Yb(OTf)_3$, $YbCl_3$, $Cs^+$, $TlMe_3$, $Tl^+$, $Tl^{3+}$, $Pd(PAr_3)_2$, $Pd(PAr_3)_2^{2+}$, $Pd^{2+}$, $Pt^{2+}$, $Cu^+$, $Ag^+$, $Au^+$, $CdR^+$, $Cd^{2+}$, $HgR^+$, $Hg^+$, $Hg^{2+}$, $B(OR)_3$, $BF_3$, $BCl_3$, $R_3Si^+$, $Si^{4+}$, $As^{3+}$, $SO_3$, $BR_3$, $BH_3$, a salt thereof, or a combination thereof, wherein at each occurrence R is independently substituted or unsubstituted $(C_1-C_{20})$hydrocarbyl.

Embodiment 20 provides the method of any one of Embodiments 1-19, wherein the electrophilic compound is a $La^{3+}$ salt.

Embodiment 21 provides the method of any one of Embodiments 1-20, wherein the electrophilic compound is $LaCl_3$, $LaBr_3$, $La(OH)_3$, or a combination thereof.

Embodiment 22 provides the method of any one of Embodiments 1-21, wherein the electrophilic compound is $LaBr_3$.

Embodiment 23 provides the method of any one of Embodiments 1-22, wherein the electrophilic compound is $LaBr_3 \cdot 6H_2O$.

Embodiment 24 provides the method of any one of Embodiments 1-23, wherein the heating the starting material to form the product composition is performed in about 0.01 min to about 100 days.

Embodiment 25 provides the method of any one of Embodiments 1-24, wherein the heating the starting material to form the product composition is performed in about 1 day to about 30 days.

Embodiment 26 provides the method of any one of Embodiments 1-25, wherein the heating the starting material to form the product composition is performed in about 1 hour to about 2 days.

Embodiment 27 provides the method of any one of Embodiments 1-26, wherein the heating comprises maintaining the starting material composition at reflux.

Embodiment 28 provides the method of any one of Embodiments 1-27, wherein the heating comprises maintaining the starting material composition at greater than about room temperature to about 300° C.

Embodiment 29 provides the method of any one of Embodiments 1-28, wherein the heating comprises maintaining the starting material composition at about 50° C. to about 130° C.

Embodiment 30 provides the method of any one of Embodiments 1-29, wherein the selectivity of the conversion of the cis,cis-muconic acid, the cis,trans-muconic acid, or a combination thereof, in the starting material composition to the trans,trans-muconic acid in the product composition is about 0.01% to about 100%.

Embodiment 31 provides the method of any one of Embodiments 1-30, wherein the selectivity of the conversion of the cis,cis-muconic acid, the cis,trans-muconic acid, or a combination thereof, in the starting material composition to the trans,trans-muconic acid in the product composition is about 50% to about 95%.

Embodiment 32 provides the method of any one of Embodiments 1-31, wherein the conversion of the cis,cis-muconic acid, the cis,trans-muconic acid, or a combination thereof, in the starting material composition is about 0.01% to about 100%.

Embodiment 33 provides the method of any one of Embodiments 1-32, wherein the conversion of the cis,cis-muconic acid, the cis,trans-muconic acid, or a combination thereof, in the starting material composition is about 50% to about 95%.

Embodiment 34 provides the method of any one of Embodiments 1-33, wherein the conversion of the cis,cis-muconic acid, the cis,trans-muconic acid, or a combination thereof, in the starting material composition is about 80% to about 90%.

Embodiment 35 provides the method of any one of Embodiments 1-34, wherein the yield of the trans,trans-muconic acid in the product composition from the cis,cis-muconic acid, the cis,trans-muconic acid, or a combination thereof, in the starting material composition is about 0.01% to about 100%.

Embodiment 36 provides the method of any one of Embodiments 1-35, wherein the yield of the trans,trans-muconic acid in the product composition from the cis,cis-muconic acid, the cis,trans-muconic acid, or a combination thereof, in the starting material composition is about 40% to about 80%.

Embodiment 37 provides the method of any one of Embodiments 1-36, wherein the aqueous solution comprises an acidic fermentation broth comprising the cis,trans-muconic acid, the cis,cis-muconic acid, or a combination thereof.

Embodiment 38 provides the method of Embodiment 37, wherein the fermentation broth comprises glucose and supports the conversion of glucose into muconic acid by yeast.

Embodiment 39 provides the method of any one of Embodiments 37-38, wherein the fermentation broth comprises yeast nitrogen base.

Embodiment 40 provides the method of Embodiment 39, wherein the yeast nitrogen base is substantially free of amino acids, ammonium sulfate, or a combination thereof.

Embodiment 41 provides the method of any one of Embodiments 37-40, wherein the fermentation broth comprises ammonium sulfate.

Embodiment 42 provides the method of any one of Embodiments 37-41, wherein the fermentation broth comprises complete supplement mixture (CSM) uracil-dropout amino acid mix.

Embodiment 43 provides the method of any one of Embodiments 37-42, wherein the method comprises at least partially simultaneously fermenting the broth to form cis, trans-muconic acid of the starting material, cis,cis-muconic acid of the starting material, or a combination thereof, and transforming the starting material composition to the product composition in the broth.

Embodiment 44 provides the method of Embodiment 1, further comprising reacting the trans,trans-muconic acid with a Diels-Alder dienophile to form a Diels-Alder adduct.

Embodiment 45 provides the method of Embodiment 44, wherein the Diels-Alder reaction is performed in DMSO without any purification or separation after the isomerization reaction.

Embodiment 46 provides the method of any one of Embodiments 44-45, wherein the Diels-Alder reaction is performed at elevated temperatures, in γ-valerolactone (GVL), or in dioxane, the dienophile is a substituted or unsubstituted ethylene, and the Diels-Alder adduct is a substituted or unsubstituted cyclohex-1-ene-1,4-dicarboxylic acid and no substituted or unsubstituted cyclohex-2-ene-1,4-dicarboxylic acid is formed.

Embodiment 47 provides the method of any one of Embodiments 44-46, wherein the dienophile is a substituted or unsubstituted ethylene, wherein the Diels-Alder adduct is a tetrahydrogenated substituted or unsubstituted terephthalic acid.

Embodiment 48 provides the method of any one of Embodiments 44-47, further comprising aromatizing the Diels-Alder adduct, to provide an aromatic compound.

Embodiment 49 provides the method of any one of Embodiments 44-48, wherein the dienophile is a substituted or unsubstituted ethylene, further comprising aromatizing the Diels-Alder adduct, to provide substituted or unsubstituted terephthalic acid.

Embodiment 50 provides the method of any one of Embodiments 44-49, wherein the dienophile is ethylene, further comprising aromatizing the Diels-Alder adduct, to provide terephthalic acid.

Embodiment 51 provides the method of any one of Embodiments 49-50, further comprising polymerizing the substituted or unsubstituted terephthalic acid with ethylene glycol, to provide substituted or unsubstituted polyethylene terephthalate.

Embodiment 52 provides the method of any one of Embodiments 49-51, wherein the aromatizing is performed using reactants comprising Pd/C.

Embodiment 53 provides the method of any one of Embodiments 1-52, further comprising esterifying the trans, trans-muconic acid and reacting the esterification product with a Diels-Alder dienophile to form a Diels-Alder adduct.

Embodiment 54 provides the method of Embodiment 53, wherein the dienophile is a substituted or unsubstituted ethylene, and the Diels-Alder adduct is a substituted or unsubstituted cyclohex-2-ene-1,4-dicarboxylic acid and no substituted or unsubstituted cyclohex-1-ene-1,4-dicarboxylic acid is formed.

Embodiment 55 provides a method of forming trans,trans-muconic acid, the method comprising:
heating a starting material composition to form a product composition comprising trans,trans-muconic acid, wherein the starting material composition comprises
cis,cis-muconic acid, cis,trans-muconic acid, or a combination thereof, and
a $La^{3+}$ salt.

Embodiment 56 provides a method of forming trans,trans-muconic acid, the method comprising:
heating a starting material composition to form a product composition comprising trans,trans-muconic acid, wherein the starting material composition comprises cis,cis-muconic acid, cis,trans-muconic acid, or a combination thereof, and
$AlBr_3$, $AlCl_3$, or a combination thereof, and a polar aprotic solvent.

Embodiment 57 provides a method of forming trans,trans-muconic acid, the method comprising:
heating a starting material composition to form a product composition comprising trans,trans-muconic acid, wherein the starting material composition comprises
cis,cis-muconic acid, cis,trans-muconic acid, or a combination thereof, and dimethylsulfoxide (DMSO).

Embodiment 58 provides a method of forming a trans, trans-muconic acid Diels-Alder adduct, the method comprising:
heating a starting material composition to form a product composition comprising trans,trans-muconic acid, wherein the starting material composition comprises
cis,cis-muconic acid, cis,trans-muconic acid, or a combination thereof, and
an electrophilic compound, a polar aprotic solvent, or a combination thereof; and
reacting the trans,trans-muconic acid with a dienophile, to form a Diels-Alder adduct.

Embodiment 59 provides a method of forming trans,trans-muconic acid, the method comprising:
heating a starting material composition to form a product composition comprising trans,trans-muconic acid, wherein the starting material composition comprises
cis,cis-muconic acid, cis,trans-muconic acid, or a combination thereof,
dimethylsulfoxide (DMSO), and
about 0 wt % to about 20 wt % water. $D_2O$, or a combination thereof;
wherein the starting material composition is substantially free of solvents other than the DMSO and the water and $D_2O$.

Embodiment 60 provides a method of cycloaddition, the method comprising:
performing a Diels-Alder reaction on a reaction mixture, the reaction mixture comprising diene trans,trans-muconic acid and dienophile substituted or unsubstituted ethylene, to form a Diels-Alder adduct, wherein
the Diels-Alder reaction is performed at elevated temperatures, in γ-valerolactone (GVL), in dioxane, or a combination thereof, and
the Diels-Alder adduct is a substituted or unsubstituted cyclohex-1-ene-1,4-dicarboxylic acid and substantially no substituted or unsubstituted cyclohex-2-ene-1,4-dicarboxylic acid is formed.

Embodiment 60 provides the method of any one or any combination of Embodiments 1-59 optionally configured such that all elements or options recited are available to use or select from.

What is claimed is:

1. A method of forming trans,trans-muconic acid, the method comprising:
heating a starting material composition to form a product composition comprising trans,trans-muconic acid, wherein the starting material composition comprises
cis,cis-muconic acid, cis,trans-muconic acid, or a combination thereof,
wherein the starting material further comprises at least one of $La^{3+}$ salt, $AlBr_3$, $AlCl_3$, and DMSO.

2. The method of claim 1, wherein the organic solvent is a polar aprotic solvent.

3. The method of claim 2, wherein the polar aprotic solvent comprises dimethylsulfoxide (DMSO), acetonitrile (CH₃CN), tetrahydrofuran (THF), ethyl acetate (EtOAc), dimethylformamide (DMF), γ-valerolactone (GVL), methanol, ethanol, 2-propanol, hexanol, toluene, or a combination thereof.

4. The method of claim 2, wherein the organic solvent is dimethylsulfoxide (DMSO).

5. The method of claim 1, wherein the starting material composition further comprises water, D₂O, or a combination thereof.

6. The method of claim 5, wherein the starting material composition is substantially free of solvents other than DMSO and the water and D₂O.

7. The method of claim 1, wherein about 0.000001 wt % to about 20 wt % of the starting material composition is water, D₂O, or a combination thereof.

8. The method of claim 1, wherein the concentration of the cis,cis-muconic acid and the cis,trans-muconic acid in the starting material composition is about 0.000001 g/L to about 350 g/L.

9. The method of claim 1, wherein the selectivity of the conversion of the cis,cis-muconic acid, the cis,trans-muconic acid, or a combination thereof, in the starting material composition to the trans,trans-muconic acid in the product composition is about 50% to about 95%.

10. The method of claim 1, wherein the conversion of the cis,cis-muconic acid, the cis,trans-muconic acid, or a combination thereof, in the starting material composition is about 50% to about 95%.

11. The method of claim 1, wherein the yield of the trans,trans-muconic acid in the product composition from the cis,cis-muconic acid, the cis,trans-muconic acid, or a combination thereof, in the starting material composition is about 40% to about 80%.

12. The method of claim 1, further comprising reacting the trans,trans-muconic acid with a Diels-Alder dienophile to form a Diels-Alder adduct.

13. The method of claim 12, wherein the Diels-Alder reaction is performed in DMSO without any purification or separation after the isomerization reaction.

14. The method of claim 12, wherein the dienophile is a substituted or unsubstituted ethylene, wherein the Diels-Alder adduct is a tetrahydrogenated substituted or unsubstituted terephthalic acid.

15. The method of claim 12, further comprising aromatizing the Diels-Alder adduct, to provide an aromatic compound.

16. The method of claim 14, further comprising polymerizing the substituted or unsubstituted terephthalic acid with ethylene glycol, to provide substituted or unsubstituted polyethylene terephthalate.

17. A method of forming trans,trans-muconic acid, the method comprising:
heating a starting material composition to form a product composition comprising trans,trans-muconic acid, wherein the starting material composition comprises cis,cis-muconic acid, cis,trans-muconic acid, or a combination thereof, and
(A), (B), or (C), or both (A) and (B):
(A) a La³⁺ salt,
(B) AlBr₃, AlCl₃, or a combination thereof, and a polar aprotic solvent,
(C) dimethylsulfoxide (DMSO), and about 0 wt % to about 20 wt % water, D₂O, or a combination thereof, wherein the starting material composition is substantially free of solvents other than the DMSO and the water and D₂O.

18. The method of claim 1, further comprising performing a Diels Alder reaction by reacting the trans,trans-muconic acid and substituted or unsubstituted ethylene, to form a Diels-Alder adduct, wherein
the Diels-Alder reaction is performed at elevated temperatures, in γ-valerolactone (GVL), in dioxane, or a combination thereof, and
the Diels-Alder adduct is a substituted or unsubstituted cyclohex-1-ene-1,4-dicarboxylic acid and substantially no substituted or unsubstituted cyclohex-2-ene-1,4-dicarboxylic acid is formed.

* * * * *